United States Patent
Haskell et al.

(10) Patent No.: US 7,667,369 B2
(45) Date of Patent: Feb. 23, 2010

(54) HIGH SENSITIVITY MICROSENSORS BASED ON FLEXURE INDUCED FREQUENCY EFFECTS

(75) Inventors: Reichl B Haskell, Nashua, NH (US);
Daniel S Stevens, Stratham, NH (US);
Jeffrey C Andle, Falmouth, ME (US)

(73) Assignee: Delaware Capital Formation, Inc., Wilmington, DE (US)

( * ) Notice: Subject to any disclaimer, the term of this patent is extended or adjusted under 35 U.S.C. 154(b) by 0 days.

(21) Appl. No.: 11/753,047

(22) Filed: May 24, 2007

(65) Prior Publication Data
US 2008/0100176 A1    May 1, 2008

Related U.S. Application Data

(60) Provisional application No. 60/863,871, filed on Nov. 1, 2006.

(51) Int. Cl.
*H03H 9/25* (2006.01)
(52) U.S. Cl. .............................. 310/313 R; 310/154.04; 310/331
(58) Field of Classification Search ................. 310/331, 310/154.04
See application file for complete search history.

(56) References Cited

U.S. PATENT DOCUMENTS

| | | | |
|---|---|---|---|
| 5,208,504 | A | 5/1993 | Parker et al. |
| 5,345,201 | A | 9/1994 | Greer et al. |
| 5,445,008 | A | 8/1995 | Wachter et al. |
| 5,719,324 | A | 2/1998 | Thundat et al. |
| 5,729,075 | A | 3/1998 | Strain |
| 5,867,074 | A | 2/1999 | Ogiso et al. |
| 6,335,667 | B1 | 1/2002 | Takagi et al. |
| 6,336,366 | B1 * | 1/2002 | Thundat et al. .......... 73/514.34 |
| 6,378,370 | B1 | 4/2002 | Haskell et al. |
| 6,539,774 | B1 | 4/2003 | Zinck et al. |
| 6,553,836 | B2 | 4/2003 | Williams |
| 6,668,627 | B2 * | 12/2003 | Lange et al. ................... 73/105 |
| 6,953,977 | B2 | 10/2005 | Mlcak et al. |

(Continued)

FOREIGN PATENT DOCUMENTS

GB    2117115    * 10/1983

(Continued)

OTHER PUBLICATIONS

Fletcher, E.D. et al., "A Comparison of the Effects of Bending Moments on the Vibrations of AT and SC (or TTC) Cuts of Quartz", Proc. 33rd Annual Symposium on Frequency Control, 1979, pp. 346-350, Philips Research Laboratories, England.

(Continued)

*Primary Examiner*—Walter Benson
*Assistant Examiner*—Bryan P Gordon
(74) *Attorney, Agent, or Firm*—Vern Maine & Associates

(57) ABSTRACT

Acoustic sensing utilizing a cantilever structure coupled about at least one side of said cantilever to a base substrate, wherein said cantilever includes a piezoelectric section and has at least one acoustic wave device on a portion of the cantilever, wherein a flexure of the cantilever produces force-frequency effects measurable by the acoustic wave device. According to one embodiment, the cantilever sensor uses the flexure-frequency effect as measured by an acoustic wave device to sense a target matter. According to one embodiment, a sensing material is disposed on at least a portion of at least one surface of the cantilever.

21 Claims, 23 Drawing Sheets

U.S. PATENT DOCUMENTS

| | | |
|---|---|---|
| 6,984,925 B2 | 1/2006 | Morley et al. |
| 7,002,281 B2 | 2/2006 | Andle |
| 2003/0119220 A1* | 6/2003 | Mlcak et al. .................. 438/52 |
| 2005/0012431 A1* | 1/2005 | Andle .................... 310/313 D |
| 2005/0034542 A1 | 2/2005 | Thaysen |

OTHER PUBLICATIONS

"Acoustic Wave Sensors", Nov. 9, 2006, [online] [retrieved on Nov. 9, 2006] Retrieved from the internet <URL://http://www.visensors.com/tech_ref/AWS_WebVersion.pdf>, pp. 1-44.

Tappura, Kirsi, "Biosensors", VTT Technical Research Centre of Finland; Apr. 2006, pp. 1-23.

Boy, J.J. et al., "Theoretical and Experimental Studies of the Force-Frequency Effect in BAW LGS and LGT Resonators", IEEE International Frequency Control Symposium and PDA Exhibition, 2001, pp. 223-226.

Kim, Yoonkee et al., "Force-Frequency Effects of Y-cut Langanite and Y-cut Langatate", IEEE International Frequency Control Symposium and PDA Exhibition, 2002, pp. 328-332.

Lukaszek, T.J. et al., "Resonators For Severe Environments", US Army Electronics Technology & Devices Laboratory, 1979, pp. 311-321.

Andle, J.C. et al., "Acoustic Wave Biosensors", Nov. 1995, pp. 1-22, Laboratory for Surface Science and Technology and Department of Electrical and Computer Engineering, University of Maine, Orono, Maine.

Arecco, Daniel, "Analysis and Preliminary Characterization of a MEMS Cantilever-Type Chemical Sensor", Dec. 17, 2003, pp. 1-220, Worcester Polytechnic Institute.

* cited by examiner

HIGH SENSITIVITY MICROSENSORS BASED ON FLEXURE INDUCED FREQUENCY EFFECTS

RELATED APPLICATIONS

This application claims the benefit of U.S. Provisional Applications No. 60/863,871, filed Nov. 1, 2006, and is herein incorporated in its entirety by reference.

FIELD OF THE INVENTION

The invention relates to sensors, and more particularly, to sensing technology involving cantilevers.

BACKGROUND OF THE INVENTION

There have been significant advances in the sensing industry based on requirements for such fields as airport security as well as military and medical applications. For example, it is broadly publicized that the airport and ship terminal screening measures for explosives, radioactive or biological dangers have been hampered by inadequate sensing equipment.

There are various types of sensors and sensing applications. Current gas sensors are typically based on mass loading of a sensing film upon exposure to a target analyte. Mass loading refers to measuring changes of the vibrating member due to on an increase of the mass caused by an adsorption of some gas. A mass loaded resonator has electrodes and the device vibrates at some resonant frequency. As the gas molecules are adsorbed by the sensing film, the added mass of the gas molecules causes a change in the propagation or resonance of the acoustic wave device (AWD). For such a device the resulting change is a frequency decrease.

Another sensing area involves cantilevers. One cantilever method employs a highly sensitive cantilever structure with optical detection based on bending of the cantilever. A further cantilever technique is a piezoresistive/piezoelectric element on the cantilever that directly senses induced strain caused by bending of the cantilever as a resistance or voltage change. However, as detailed herein, these prior systems fell far short of the customer requirements in the expanding array of sensing applications.

Some examples of the current art are described herein in general terms for illustrative purposes. Referring to FIG. 1a, which is a capacitance-based platform disposed in a package, typically a microelectromechanical (MEMS) capacitive diaphragm sensor. Disposed upon the substrate 5, there is a lower plate 20 and a vented upper plate 10 with a central fill hole 25. A polymeric sensing film 30 is disposed between the lower plate 20 and the upper plate 10. Electrical connectivity is provided by the lower plate electrical connector 15 that allows the energy source and response measurement connections. Typically these devices use thick film polymer sensing films to form a sensor array. As known to those in the art, there is a change in the dielectric constant of polymers upon exposure, thereby allowing detection. In this capacitive sensor design, there generally is a consistent gap width between the plates and a good baseline. Such a system is typically low in power and there is no pre-concentrator.

FIG. 1b depicts a SiC resonator which typically is constructed in a sensor array, such as 2-5 microns, and uses mass loading for detection. The piezoelectric low frequency MEMS structure in FIG. 1b illustrates a P-type silicon substrate 40 upon which is disposed an N-type material 45, such as SiC. Not only is the substrate 40 covered by the N-type material 45, but the N-type material 45 extends outwardly from an end of the substrate 40 creating an extended type structure which shall be termed a cantilevered beam. An epitaxial piezoelectric layer (AlN) 50 is disposed on portions of the P-type silicon substrate 40, including portions on the cantilevered beam. An upper electrode 55 is disposed upon the epitaxial piezoelectric layer 50. A lower electrode contact 35 is coupled to the N-type layer on a portion above the substrate 40 without extending onto the cantilevered beam. This structure may include a pre-concentrator to increase sensitivity, but takes further time to collect samples, such that they generally do not operate in real time. This typically uses thick film polymers and subject to polymer thickness control issues. The resonator is more prone to Q and temperature stability issues. It is also not energy efficient with power spikes for required heating of the pre-concentrator. For illustrative purposes, a further description of this general type of device can be found in U.S. Pat. No. 6,953,977.

FIG. 2a illustrates a surface acoustic wave (SAW) delay line structure commonly used for sensing applications. This two port structure serves as a gas sensor by placing a gas specific sensing film 65 on the surface of the device in-between an input transducer 60 and an output transducer 70 which is disposed upon a piezoelectric SAW substrate 75. When the sensing film 65 gets exposed to a gas, mechanical and electrical perturbations of the sensing film 65 causes a corresponding change in the propagation characteristics of the AWD. When the SAW structure is coupled to an oscillator circuit, the result in an increase or decrease in oscillator frequency. Some examples of sensing films can be metal, metal oxide, metal nitride, metal carbide, polymer, fluoropolymer, silane, siloxane, silicone, or biological material (antigens, bacterial biofilms, biopolymers, or cell cultures). In certain combinations of films and device structures it is possible to extend the sensing film over the entire device or to employ the device conductors or substrate as the sensing medium. In addition to delay lines SAW resonators also exist. Prior SAW resonators include those described in U.S. Pat. No. 6,335,667 and the multi-reflective AWDs as disclosed in U.S. Pat. No. 7,002,281. There are numerous other waves related to the SAW in their use of similar transducers, called surface generated acoustic wave (SGAW), and these terms shall be deemed interchangeable.

The SGAW-based platforms such as those illustrated in FIG. 2a typically have thick film polymers forming the sensor array. The sensing film is in the delay path and employs mass loading to detect change in frequency. A pre-concentrator can be used to increase sensitivity however the heating can cause high power spikes and is less energy efficient.

There are also known systems that measures displacement of a cantilever using optics. Referring to FIG. 2b, a MEMS cantilever system with optical detection is depicted in which the mechanical resonance of a mechanical structure is employed. This type of system generally employs a silicon substrate which is not a piezoelectric material. The silicon substrate 80 has a cavity portion 100 and the structure includes layers about the periphery of the device, including a cantilever 85 extending from an end of the device. There is a sensing film 95 disposed upon a film surface 90 wherein the film surface 90 relates to attachment chemistry for disposing a sensing film 95, which is typically a metallization layer.

The silicon MEMS cantilever assembly 85 is typically coupled with a piezoelectric transducer or electrostatic driver (not shown) that is driven with an oscillator (not shown) to vibrate at the mechanical resonance of the cantilever 85. The laser diode 105 emits a laser beam signal 110 that reflects off the cantilever surface to the detector 115. The measured response can be used to lock that relative frequency and it can detect changes from that relative frequency. Alternatively, it may be able to measure the difference between the frequency of the driving oscillator and the actual measured frequency.

Induced bending of the cantilever is in resonance mode and it uses a bi-cell detector 110 that measures the frequency and may also measure bending effects for resolution. This optical cantilever system measures the change of the angle of deflection of laser light 110 typically from a laser diode 105. The laser light 110 incident upon the end of the cantilever 85 typically bounces off the end of the cantilever and is received at an optical detector 115 such as a bi-cell optical detector. As gas affects the sensing film 95, there is a change to the cantilever 85, and the optical detection 115 measures changes to the angle of deflection of the laser light 110 bounced off the end of the cantilever 85. While complicated, the stress induced effects on the cantilever 85 combined with the optical detection provides satisfactory sensitivity. Nonetheless a simpler, more robust system is desired, as is better sensitivity and resolution.

In sum, sensors of this type typically measure changes in bending of the cantilever or changes in resonant frequency of the mechanical structure. A change in the bending or strain of the sensing film translates into a direct change in the shape of the cantilever which is then measured by the optic detection system. Another approach uses changes in film mass or stiffness of sensing film to affect the overall spring mass constant of the cantilever altering its resonant frequency. In this resonance system, the cantilever needs a piezoelectric transducer and oscillator or electrostatic means to drive the unit in addition to the optical detection mechanism. Sensors of this type are controlled by the exact shape and resonant frequency of the cantilever itself, limiting the design and implementation and incurring direct damping of the cantilever resonant Q by the sensing film. For illustrative purposes, U.S. Pat. Nos. 5,719,324 and 5,445,008 describe background information for sensors of this type.

While sensing platforms are available, the industry demands a sensing technology that has a significant improvement in sensitivity and simplicity over existing sensing technologies.

SUMMARY OF THE INVENTION

The present invention according to one embodiment relates to sensing technology based on geometric response to film induced stress.

One embodiment of the present invention is a system for acoustic sensing, comprising a cantilever structure coupled to a substrate about at least one side of the cantilever, wherein the cantilever includes a piezoelectric section and has at least one AWD on a portion of the cantilever. A flexure of the cantilever produces flexure-frequency effects measurable by the AWD.

The system may also include a sensing material disposed on at least a portion of at least one surface of the cantilever. The sensing material can be, for example, metal, metal oxide, metal nitride, metal carbide, ceramic, carbide, polymer, fluoropolymer, silane, siloxane, silicone, or biological material, by way of nonlimiting example.

According to one embodiment, the active acoustic region is a thickness field excitation (TFE) structure formed by at least one positive electrode disposed on one side of the cantilever and at least one ground electrode on an opposing side of the cantilever, and wherein an electrical energy source is coupled to the positive electrode and the ground electrode. TFE structures include thickness shear mode (TSM) resonators, thickness twist mode resonators, thickness extensional mode resonators, face shear mode resonators and length extensional mode resonators. Traditional bulk material may be machined or thin film, and methods such as the film bulk acoustic resonator (FBAR) may be employed.

A variation of the thickness field excitation (TFE) structure is a two port device wherein a first transducer is electrically coupled to the electrical energy source by a positive electrical connection and a negative electrical connection and a second transducer provides a response related to the input electrical signal from the electrical energy source to a second positive electrical connection and second negative electrical connection. Often the negative electrical connections and electrodes are cojoined into a single, common "ground" or negative connection and electrode.

In another embodiment, the AWD is a lateral field excitation (LFE) structure formed by at least one positive electrode and at least one negative electrode electrically coupled on one side of the cantilever and to an electrical energy source. While LFE differ from TFE in the orientation of the applied electric field, the entire range of allowed resonators can be potentially implemented, as noted herein. LFE and TFE share the common feature that electric fields applied within the bulk of the piezoelectric material excite acoustic energy throughout the bulk of the material and collectively these are known as bulk acoustic wave (BAW) structures.

The system according to another embodiment wherein the AWD is a surface generated acoustic wave (SGAW) structure formed by at least one transducer electrically coupled on one side of the cantilever, wherein the transducer is electrically coupled to an electrical energy source. The system can further include a surface displacement medium operatively coupled with the transducer, wherein the surface displacement medium can be any of: reflective grating, delay line, metal trapping grating, and thin film trapping layer. Note that "thin" is not meant to convey a specific thickness or application process and that so-called "thick film" coating methods are still contemplated as thin film trapping layers according to one embodiment.

The SGAW can be a one port device wherein a single transducer is electrically coupled to the electrical energy source by a positive electrical connection and a negative electrical connection.

Another variation of the SGAW is a two port device wherein the first transducer is electrically coupled to the electrical energy source by a positive electrical connection and a negative electrical connection and the second transducer provides a response related to the input signal from the electrical energy source to a second positive electrical connection and second negative electrical connection.

The shape of the cantilever in accordance with one embodiment is rectangular whole, rectangular half, square whole, square half, circular whole, circular half, oval whole, oval half, triangular whole, triangular half, polygonic whole and polygonic half.

The cantilever can be coupled to the substrate by a single tether, single fixed support, dual tether, dual fixed support, or more complex geometries.

A measurement device can be coupled to the AWD and measuring the flexure-frequency effects. Measurement devices are, by way of non-limiting example, devices that measure the phase, frequency, spectral signature, pulse shape, amplitude or other characteristic or modulation of the electrical signals within the AWD or presented at the electrical connections. Where the term frequency is used in conjunction with a measurement or observation it is implicit that any other characteristic of the signal could be implied. Therefore the term flexure-frequency should also be broadly construed as meaning the effect of flexure and related strain in the cantilever on any of the characteristics of the electrical signal chosen for measurement, and frequency merely being one of the most widely employed characteristics in AWD sensors.

According to another embodiment a method for detecting a target substance includes forming a piezoelectric cantilever having at least one AWD disposed about a portion of the cantilever, exposing the cantilever structure to some environment, causing a flexure response of the cantilever from the environment and detecting a response of the AWD.

An addition step includes disposing a sensing material on at least one portion of the cantilever and allowing adsorption/absorption of the target substance by the sensing material.

Another step includes aligning the AWD at an angle ($\psi$) from a defining crystallographic axis and/or from the defining axis of the cantilever for a maximum change in frequency or other measured signal property.

According to one embodiment, there is a sensing device for measuring flexure-frequency effects, including a substrate having electrical connections disposed about the substrate and providing connectivity to an electrical energy source and a measurement device. A cantilever is coupled on one side to the substrate. The cantilever includes at least one AWD formed on a portion of the cantilever, wherein the AWD comprises a piezoelectric section with at least two electrodes disposed thereon. A flexure of the cantilever causes a signal change of the AWD that is measurable by the measurement device. The sensing device may further comprise a sensing material disposed on at least a portion of at least one surface of the cantilever. Typically the sensing film will enhance the selectivity and sensitivity of the flexure of the plate to a target environmental condition being monitored by the sensor.

The sensing device can be any sensor such as bulk acoustic (BAW) cantilever gas sensors, BAW cantilever magnetic sensors, BAW cantilever torque sensors, surface acoustic wave (SAW) cantilever gas sensors, SAW cantilever magnetic sensors, SAW cantilever gas sensors, monolithic crystal filter (MCF) cantilever gas sensors, MCF cantilever magnetic sensors, MCF cantilever torque sensors, film bulk acoustic resonator (FBAR) cantilever gas sensors, FBAR magnetic sensors, and FBAR torque sensors.

The material for the piezoelectric section can be selected from any of the available piezoelectric crystals and poled ceramics, by way of non-limiting example including: quartz, lithium niobate, lithium tantalate, langasite, langanite, langatate, aluminum phosphate, gallium phosphate, calcium/strontium niobium/tantalum gallium silicate (CNGS, CTGS, SNGS, and STGS), zinc oxide, aluminum nitride and compositions or combinations thereof.

Yet a further embodiment is a system for acoustic sensing, comprising a cantilever structure coupled to a substrate about at least one side of the cantilever, wherein the cantilever includes a piezoelectric section and having at least one AWD, wherein the AWD occupies only a portion of the cantilever such that the design requirements of the AWD are decoupled from those of the cantilever. There is an electrical signal coupled to the AWD wherein a flexure of the cantilever produces flexure-frequency effects measurable by the AWD; and wherein the flexure-frequency effects induce modulation of the electrical signal.

According to one embodiment, a cantilever sensor design measures flexure induced frequency change of an AWD. The sensor measures the flexure of the cantilever induced by a target matter, such as a gas, wherein the gas molecules accumulate on a sensing film affixed to only a portion of the cantilever. Bending of the cantilever is measured by the flexure-frequency effect of the cantilever material on a supported AWD having a resonant frequency and Q independent of the specific cantilever geometry. The separation of cantilever design and AWD design allows for a robust and highly sensitive sensing system based on the electrical response of the supported AWD to geometrical changes of the cantilever under film induced strain.

BRIEF DESCRIPTION OF THE DRAWINGS

A fuller understanding of the invention can be gained from the following description when read with the accompanying drawings.

DETAILED DESCRIPTION

Figure 1A:
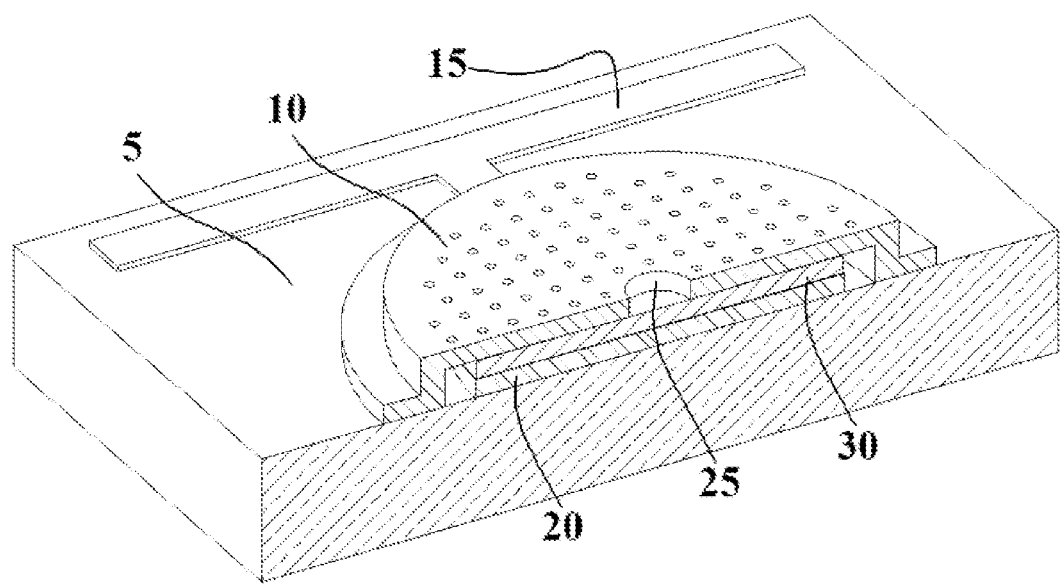
FIG. 1a is a prior art sensor for the capacitance-based platform.
Figure 1B:
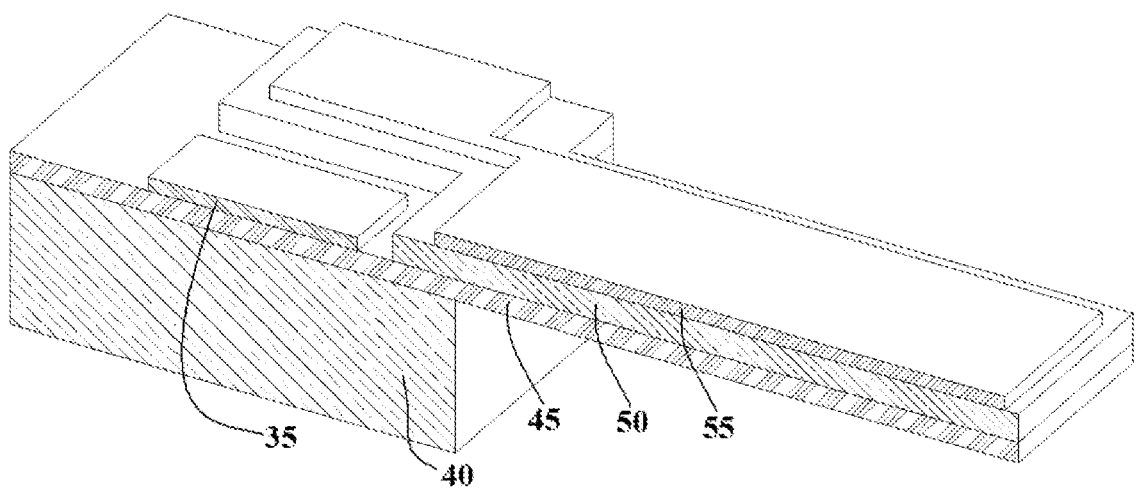
FIG. 1b is a prior art microelectromechanical (MEMS) resonator sensor.

A broad objective of the present invention is to improve sensitivity of sensor technologies by employing piezoelectric cantilevers. According to one embodiment, some of the improvements are based on the cantilever's geometric response to film induced flexure/strain when exposed to a target substance.

The piezoelectric cantilever in one embodiment utilizes the fact that the resonating active acoustic wave regions of an AWD supported on or near the cantilever will respond to the flexure induced strain (and geometric change in the cantilever), caused by the increase or decrease in film stress when a sensing film along the length of the cantilever is exposed to some influence such as a target gas. The sensing film will experience an increase or decrease in internal stress causing the cantilever to bend (geometry change and strain) and this will, in turn, cause a corresponding change in frequency in the acoustically distinct AWD fabricated thereon, termed the active acoustic regions.

Background information about resonator forces and stress, including force frequency or flexure frequency with thickness shear mode (TSM) devices, are detailed in the commonly assigned U.S. Pat. No. 6,984,925, entitled Low Acceleration Sensitivity Mounting Structures for Crystal Resonators and hereby incorporated by reference for all purposes. As is known, TSM devices are sensitive to force-frequency and flexure-frequency effects. The U.S. Pat. No. 6,984,925 according to one of the embodiments teaches orienting structures at optimal angles to minimize the effect of stress coupled to the device.

In one embodiment, stress within the sensing film induces bending of the cantilever, which causes strain-induced frequency change in the AWD, e.g. a TSM resonator. In this embodiment, an internally-generated stress in the film induces the strain (flexure) of the cantilever. As used herein, TSM devices include thickness-field excitation (TFE) devices, lateral field excitation (LFE) devices, and monolithic crystal filter (MCF) devices. Other modes are generally allowed and analogous, including face shear modes, torsional modes, length extensional modes and thickness twist modes. For operation in air or vacuum the concepts and claims herein also apply to thickness extensional mode and should be considered to be inclusive of these and other bulks acoustic wave (BAW) modes as is traditionally defined.

It is known that BAW devices can be very sensitive to flexure, namely strain, applied to the resonating quartz structure. See for example E. D. Fletcher and A. J. Douglas, "*A comparison of the effects of bending moments on the vibrations of AT and SC (or TTC) cuts of quartz*" Proc. 33$^{rd}$ Annual Symposium on Frequency Control, pp. 346-350, 1979.

Traditional lower frequency BAW devices (i.e. thickness shear mode (TSM) less than 20 MHz) suffer from two disadvantages when they are configured as mass loading sensors. The first disadvantage is the extremely low operating frequency. For acoustic wave sensors, a general rule of thumb is that the mass sensitivity is a function of frequency-squared. Thus, a 100 MHz TSM device will theoretically be 100 times more sensitive than a 10 MHz TSM device. This sensitivity increase is typically not realized since the frequency stability rapidly deteriorates with increased frequency when low-Q polymer films are placed in acoustically active locations. The direct measurement of the added mass through its effect on the resonant frequency is thus limited in practice and it is an object of this invention to allow a high frequency AWD to operate with optimized frequency stability (high Q) while still allowing the frequency to be perturbed by the sensing film—analyte interaction with optimized sensitivity.

Another disadvantage is that the change in frequency of the sensor is limited by the amount of mass that gets adsorbed onto or absorbed into the sensing film. Lower frequency TSM devices are generally large in size. The required amount of analyte scales at least as $1/F^2$ through area considerations above and beyond the $F^2$ sensitivity to mass per unit area.

Surface generated acoustic wave (SGAW) devices include several specific classes, such as surface acoustic waves (SAW) devices, surface transverse waves (STW) devices, surface skimming bulk wave (SSBW) devices, pseudo-surface acoustic wave (PSAW) devices, leaky surface acoustic wave (LSAW), Love wave devices, Lamb wave devices, Bleustein-Gulayev wave, and liquid guided acoustic wave (LGAW) devices, and Acoustic Plate Mode (APM). As used herein and unless limited elsewhere, AWD shall be designated in a broad sense to include any such device that operates whether as a resonator, filter or delay line, and is not limited to a particular material, shape or cut. Like BAW devices, in certain embodiments the disadvantage of the SGAW devices is that the change in frequency of the sensor will be limited by the amount of mass that gets adsorbed onto or absorbed into the sensing film.

It has also been shown that elastic film changes on non-acoustic wave cantilevers can create sensor platforms with much higher sensitivity than the same cantilever structures configured to respond to mass loading when exposed to a target gas. See for example, T. Thundat, E. A. Wachter, S. L. Sharp, R. J. Warmack, "*Detection of Mercury Vapor Using Resonating Microcantilevers*", Appl. Phys. Lett., 66, 13, 1995; and http://www.time.com/time/magazine/article/0, 9171,570260,00.html. These structures again have the general limitations that the cantilevers themselves are the resonant structure, incurring manufacturing and environmental variability, and that the sensing film directly loads the acoustic wave.

In one embodiment, the present invention uses the force-flexure effect from the cantilever as measured by the AWD to sense the target matter, such as a gas, wherein the gas molecules accumulate on a sensing film affixed to at least a portion of the cantilever.

By way of explanation, the sensing film is typically selected for a particular type of gas or gases, which may be sensitive to some gas(es) and not others. One example for detecting Hg, is the use of a Au film that picks up Hg and forms an amalgam. As the Hg is adsorbed on the Au sensing film, the sensing film generates film stresses causing the cantilever to bend. The rate at which the Hg sticks to the surface changes the rate at which the supported BAW resonator's frequency changes. The amount of the Hg that sticks to the surface is concentration dependent and changes the magnitude of the response. Thus the structure can detect different concentrations of the sensed gas(es).

A further embodiment of the present invention refers to using the cantilever structure to monitor externally generated strain or flexure of the cantilever, for example, to measure the induced deflection of the cantilever by "static" or "low frequency" magnetic, electric or acoustic (pressure) fields. The new standard frequency control products and etched structures demonstrate better spurious mode suppression and/or better frequency versus temperature performance due to less influence of packaging stresses on the free standing, etched microstructures. Although certain embodiments make reference to gas measurements, the present invention is not limited to gas sensing and can be used for liquid sensing as well as physical sensing.

It should be noted that, unlike traditional cantilevers, it is not necessarily the shape or dimension of the cantilever that determines the operating frequency of the resonator. The cantilever as a whole is not the resonating element and merely provides a support on which to introduce flexure of the resonator (active acoustic region) such as a photolithographically defined trapped-energy resonator or delay line. The AWDs with their corresponding active wave regions reside on only a portion of the cantilever which is less than the dimensions of the entire cantilever and lie within the edges of the cantilever, but may straddle the boundary between the cantilever and the substrate to which it is coupled.

Figure 2A:
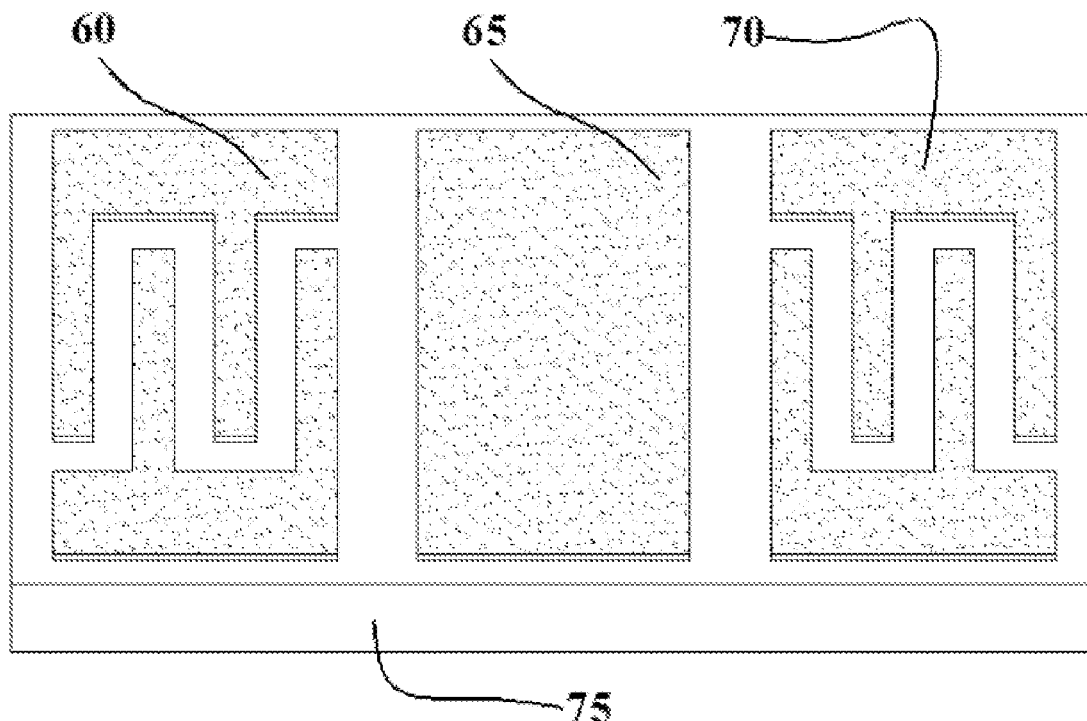
FIG. 2a is a prior art surface generated acoustic wave (SGAW) delay line.
Figure 2B:
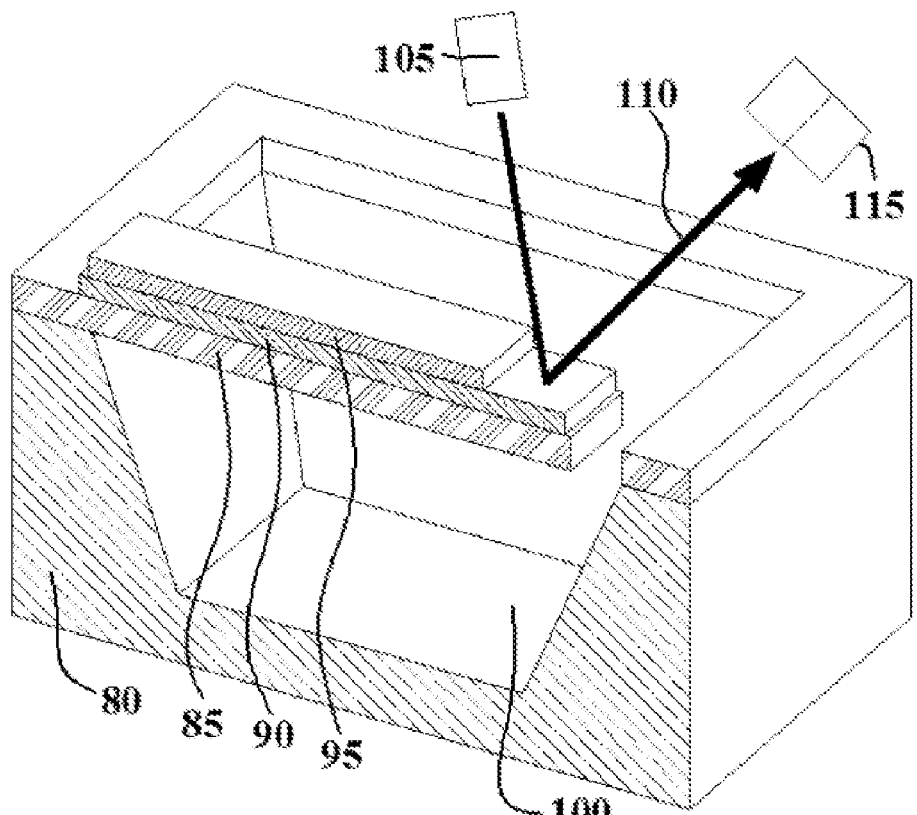
FIG. 2b is a prior art optical cantilever-based platform.
Figure 3A:
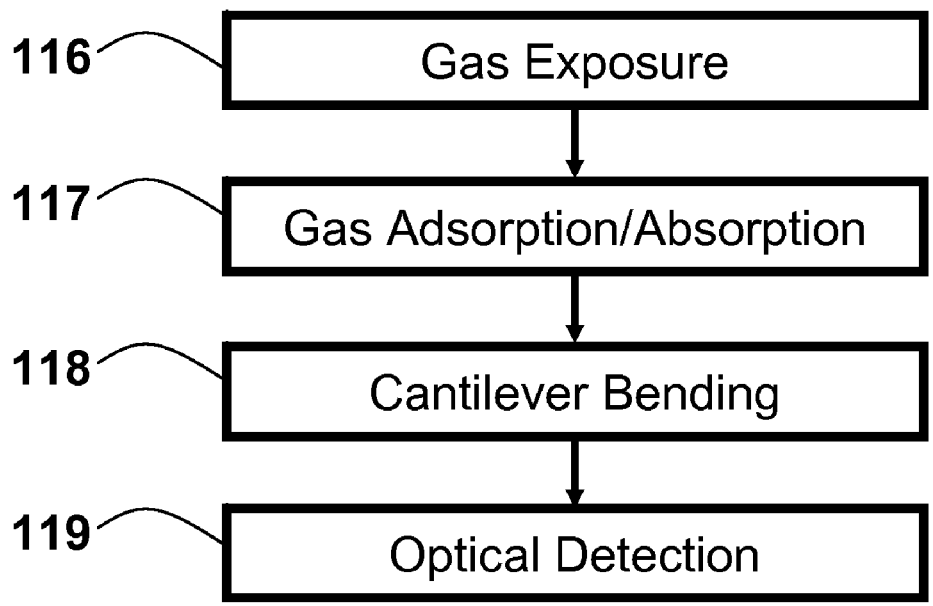
FIG. 3a is a prior art basic flowchart of the operation of an optical detection cantilever-based device.

Referring to FIG. 3a, the basic operation for a prior art MEMS optical cantilever based sensing platform described in FIG. 2b is presented. This example is a film stress based example that causes cantilever bending. In this gas sensing example, following the gas exposure 116, there is a polymer film adsorption 117. The adsorption of the gas with the sensing film causes the freely-supported cantilever to bend due to changes in the film stress. The cantilever bending 118 causes an impinging laser beam to deflect and allows for a highly sensitive measurement based on the optical detection 119. This is a direct measurement scheme.

The state of the art includes mechanical resonant frequency systems that are dependent on the mechanical geometry of the cantilever. For sensing applications, changes in a sensing film on the cantilever can cause changes in the spring constant of the mechanical cantilever causing the mechanical resonant frequency to increase or decrease depending on the type of sensing film response (i.e. mass loading versus elastic stiffening).

Another known related effect is cantilever static bending. Static bending is not necessarily related to the cantilever mechanical resonant frequency, rather, the static bending is caused by a build up of film stress when the sensing film is exposed to a target gas. This stress causes the mechanical cantilever to bend in order to restore the equilibrium of force/stress and the amount of bending is measured optically. For reference purposes, U.S. Pat. No. 6,336,366 provides some additional background information.

Figure 3B:
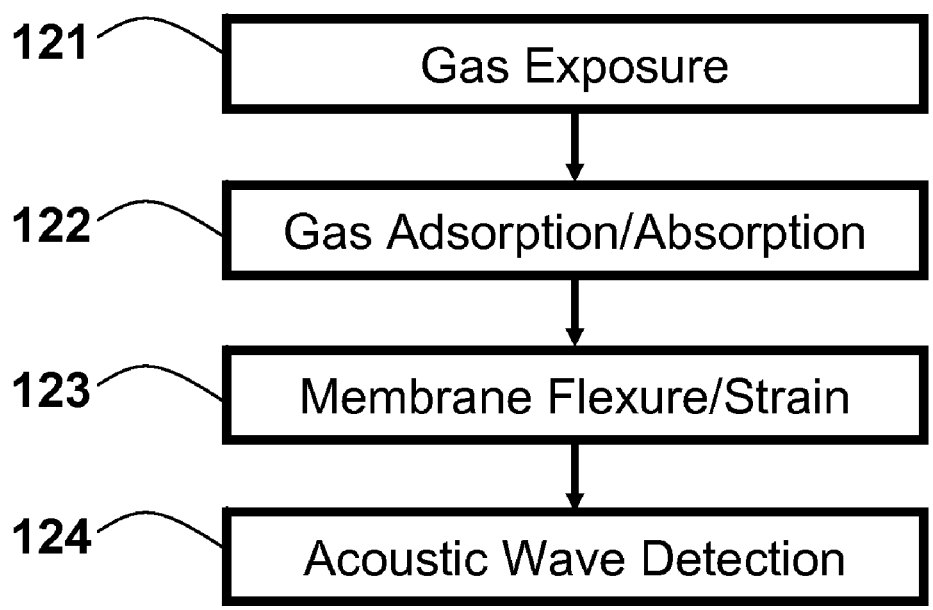
FIG. 3b is a basic flowchart of the operation of an acoustic wave detection cantilever-based device according to one embodiment.

With respect to FIG. 3b, one embodiment of the acoustic wave detection is shown. In this gas sensing embodiment, a cantilever having one or more acoustic wave detectors with a sensing film is subject to gas exposure 121. There is some gas adsorption/absorption 122 which causes a change in the flexure/strain of the membrane 123. This result is measured based on acoustic wave detection 124. By way of example, a frequency change due to the flexure is measured and processed to determine the influence of the target substance.

For reference purposes, a cursory description of adsorption (mass loading) refers to the collection of a target material on the surface of a sensing material. When a sensing film gets exposed to a gas of interest, the gas molecules will either collect on the surface (adsorb) or diffuse into the bulk of the sensing film (absorb). The effect of adsorption usually only results in mass loading and the result is a decrease in piezoelectric resonant frequency of a piezoelectric (such as BAW, SGAW, FBAR, LFE) resonator structure. For delay line structures (i.e. SAW delay line), the surface collection of mass will cause a reduction in velocity of the wave as it propagates from input IDT through the sensing film to the output IDT (this decrease in velocity results in a change in phase). For the case of a non-piezolectric mechanical cantilever, the adsorption (surface collection) effect should also be mass loading and a decrease in mechanical resonant frequency.

The effects of absorption (diffusion into the film) will cause a change in the volume of the film due to expansion as the extra gas molecules diffuse into the bulk of the sensing film. This change in sensing film volume causes a build up of film stress that will generally cause the film to want to expand both vertically and horizontally. The vertical component has little effect on any of the structures, however, the horizontal component of film dimensional change causes three main effects, namely flexure, stiffness, and in-plane stress. The first effect, flexure, will occur on structures that are free to move in response to film expansion and the second effect, elastic stiffness, will typically occur on both cantilevers and clamped structures, while the third effect will occur mainly on clamped structures.

The flexure effect relates to absorption wherein the expansion of the film will cause all cantilevers to bend in response to the film stress and its need to equilibrate. After the cantilever stops bending, the result is a net zero stress across the structure because the final film stress equals but opposes the cantilever stress required to hold the cantilever in its final bent position. This bending is called flexure. There are notable distinctions between the acoustic wave case and the mechanical cantilever implementations, namely the mechanical cantilever bends and will cause a change in the shape of the cantilever and a large displacement of the vertical position of the end of the cantilever. In the prior art, the cantilever displacement is typically measured optically.

The acoustic wave resonances of the AWDs disposed upon the cantilevers in embodiments of the present invention are dependent on the piezoelectric thickness for BAW, the IDT and reflector design properties for SGAW, piezoelectric thickness for LFE and thickness/gap for MCF. The cantilever bending causes strain which is detected by the AWD, in particular, strain causes density changes and dimensional changes of the AWD.

The absorption (diffusion into) of the film can cause the sensing film to increase in stiffness, appropriately called the elastic stiffening effect. For the prior art cantilevers, the increase in film stiffness will cause an increase in the cantilever spring constant. This increase in spring constant causes the mechanical resonant frequency to increase. The mechanical cantilever spring constant changes and the mechanical resonant frequency increases. The sensitivity of this effect is less than the effect of measuring displacement of a bent cantilever.

Similarly, for AWDs, with or without etch relieved structures, this increase in film elasticity will cause an increase in the piezoelectric resonant frequency (for resonators) or an increase in velocity resulting in a change in phase for delay line structures. However this effect is small compared to the strain based changes of the AWDs.

For AWDs in gas sensor applications, there are mechanical and electrical effects that cause changes. The mechanical effects include mass loading and elastic stiffening or softening. As gas adsorbs onto or absorbs into the sensing film, it also changes the intrinsic stress of the film on the surface of the device, causing the free cantilever to bend. In one embodiment the TSM device and the cantilever are two separate elements. The cantilever bends, changing the shape of the cantilever and the TSM device detects the bending due to flexure frequency effects. This type of arrangement can be utilized for flow sensing where an impinging flow stream directed perpendicular to the cantilever structure will cause either a direct bending (flexure) of the cantilever or cause the cantilever to vibrate and thus modulate the frequency or phase of the AWD's electrical signal transmission with the impinging signal such as a flow or vibration. For example, in one embodiment, the AWD has a frequency of operation and by flexing the membrane it changes the frequency. If the membrane is vibrated an associated oscillator circuit can be frequency modulated or phase modulated. There are numerous applications for such a device such as vibration detection, magnetic sensing, and communications.

According to one embodiment, the acoustic wave mode exists within a portion of that cantilever structure defined by the AWD. The cantilever structure itself uses a piezoelectric material and there is no need to apply a separate piezoelectric layer. Unlike the MEMS configuration detailed herein, the AWD operation is not necessarily dependent upon the sensing film or cantilever spring constant.

According to one embodiment of the present invention, the piezoelectric resonant frequency or piezoelectric design frequency is not dependent upon the geometry of the cantilever (flexure) structures. These systems are dependent on other AWD design criteria and as long as the cantilever structure is of sufficient length and width compared to the AWD to support a satisfactory resonator or delay line, the actual geometry of the cantilever is not relevant in the processing. Thus, the AWD does not require any knowledge of the cantilever. It only responds to mass directly on the active acoustic area or forces, stress, and strain applied to the acoustic active area that may be caused by the cantilever or other stress/strain causing structure.

There are several illustrative examples and embodiments for the various designs noted herein. In the BAW (e.g. TSM or FBAR) resonator example, resonant frequency is typically determined by the plate thickness, top/bottom electrodes and overlap of top and bottom electrodes. Mass on the active area or stress or strain applied to the active acoustic area will result in a change in the resonant frequency.

For the MCF (TSM) filter, the design frequency is determined by the plate thickness, the overlap of top input and ground, the overlap of top output and ground, and the gap in between the input and output electrodes. Mass over the active area or stress or strain applied to the active acoustic area will result in changes to the transmission of BAW energy from the input TSM to the output TSM.

Resonant frequency for the LFE (e.g. TSM or FBAR) resonator is generally determined by the plate thickness, the input and output electrode, and the gap between the input and output electrode. Mass over the active area or stress or strain applied to the active acoustic area will result in changes to the resonant frequency of the LFE structure.

In the SGAW resonator, the resonant frequency can be determined by the one-port or two-port IDT periodicity/electrode structure, the grating (reflector) structure, and the effective cavity length. Mass over the active area or stress or strain applied to the active acoustic area will result in changes to the resonant frequency of the one-port or two-port SGAW structure.

The SGAW delay line design frequency is typically dependent on the two-port IDT periodicity/electrode structure. Mass over the active area or stress or strain applied to the active acoustic area will result in a change in the transmission of SGAW energy from the input IDT to the output IDT. The resonant frequency of the acoustic plate mode (APM) resonator is typically determined by the two-port IDT periodicity/electrode structure, the grating (reflector) and the piezoelectric plate thickness. Mass over the active area or stress or strain applied to the active acoustic area will result in changes to the resonant frequency of the APM structure.

With respect to the FPW resonator, the resonant frequency is determined by the thin film piezoelectric thickness and the top and bottom electrode geometry. Mass over the active area or stress or strain applied to the active acoustic area will result in changes to the resonant frequency.

Figure 4A:
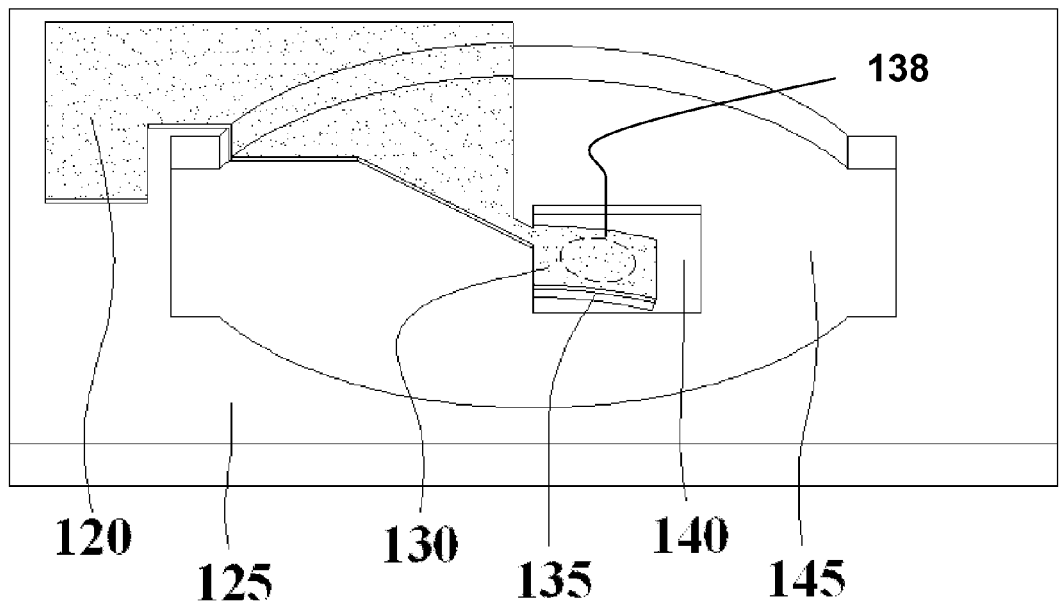
FIG. 4a is a top perspective view of a half rectangle bulk acoustic wave (BAW) structure without a sensing film according to one embodiment of the present invention.
Figure 4B:
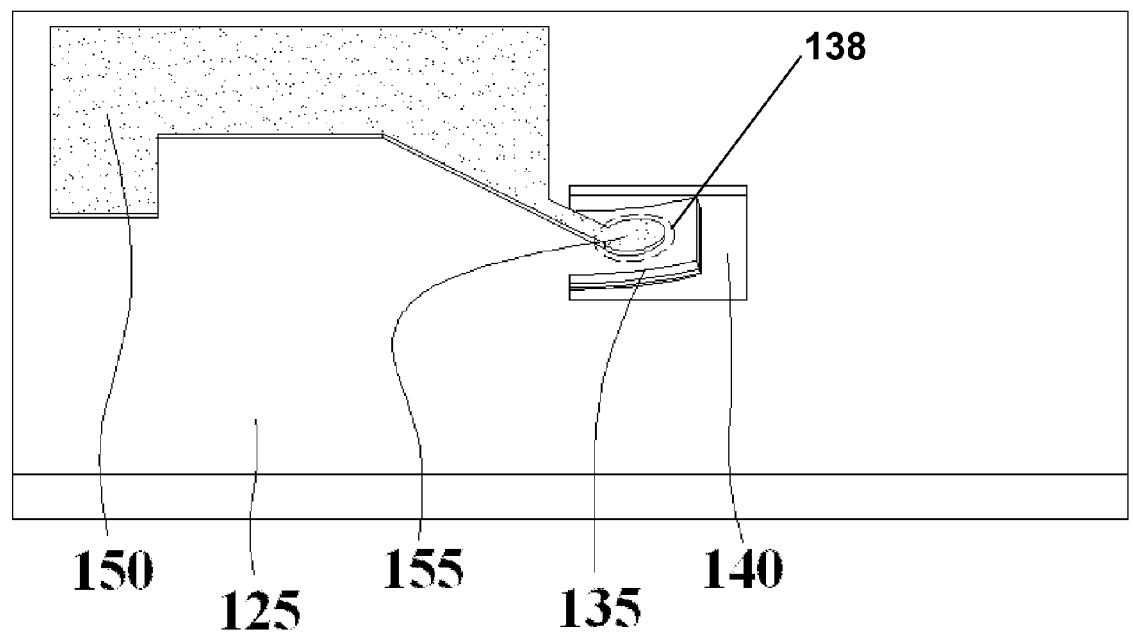
FIG. 4b is a bottom perspective view of the half rectangle bulk acoustic wave (BAW) structure of FIG. 4a according to one embodiment of the present invention.
Figure 4C:
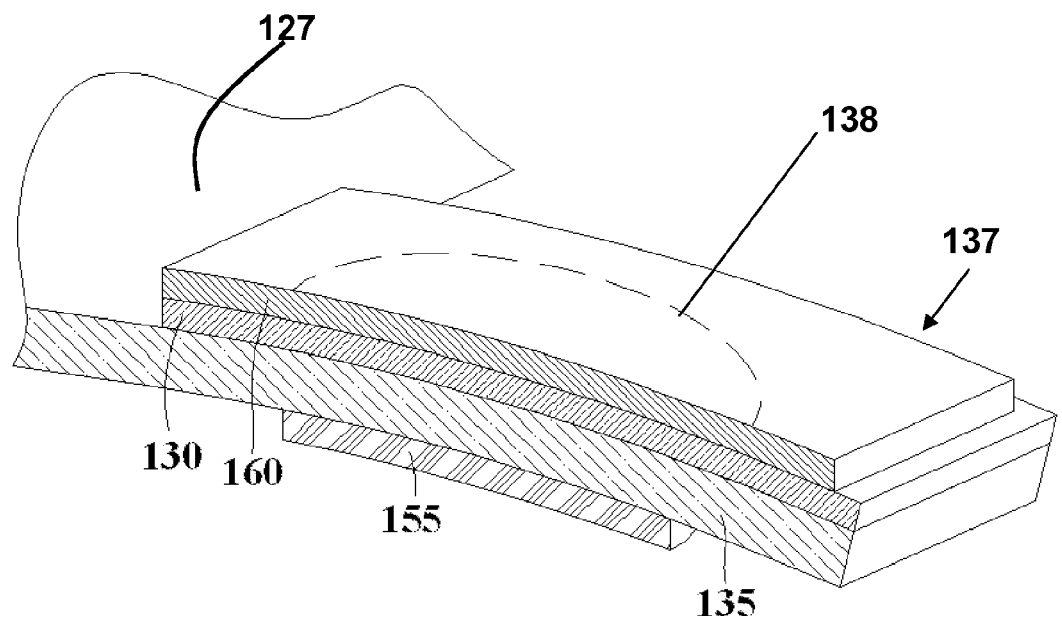
FIG. 4c shows a cut-away side perspective view of a half rectangle bulk acoustic wave (BAW) structure according to one embodiment of the invention.

Referring to FIGS. 4a, 4b, and 4c a half rectangle acoustic wave detector structure is depicted. The structure substrate 125 is a piezoelectric material with a ground electrical connection 120 disposed thereon on one side and a positive electrical connection 150 on the opposing side. There is an etched pocket area 145 with a shape that depends upon the application and packaging considerations. An etched relief region 140 is proximate the cantilever 137 and helps define the peripheral bounds of the cantilever 137.

The AWD in this embodiment is formed by the ground electrode 130 on one side of the piezoelectric diving board 135 and a positive electrode 155 on the other side, which in combination forms the AWD, referred to as a thickness field excitation (TFE) device, most commonly a TSM resonator. In a general sense, TSM refers to the effect that occurs when there is a piezoelectric material disposed between a ground electrode and a positive electrode on a device with properly selected substrate material and orientation such as AT quartz or Y-cut langasite. Application of a signal to the electrodes causes excitation of a thickness shear mechanical resonance. The intrinsic film stress of the sensing film induces flexure of the AWD. Depending on the details of the AWD, the resulting flexure may directly alter the AWD response or non-linear elasticity and density changes of the substrate may indirectly alter the AWD response during the induced flexure. Neither effect requires the sensing film to directly load the AWD's acoustic energy, although there is no specific prohibition. In at least one embodiment, no sensing film is required.

The ground electrode 130 is coupled to the ground electrical connection 120 while the positive electrode 155 is coupled to the positive electrical connection 150. It should be noted that the active acoustic area 138 is the overlapping region of the electrodes 130, 155 with the piezoelectric section 135 which forms the AWD. The active acoustic area 138 is shown only for illustrative purposes as the shape and dimensions of the active acoustic area 138 has fringes and will typically not be as linear. The sensing film 160 is disposed on at least a portion of the cantilever and in the most practical case, covers a portion of the ground electrode 130. In this embodiment, the piezoelectric diving board 135 is attached to the piezoelectric substrate 125 by a fixed mount 127 with an etched relief 140 that helps in defining the periphery of the cantilever 137. The fixed mount 127 typically is dimensioned to provide proper support for the fixed end of the half-rectangle cantilever but does not constrain the overall motion of the remainder of the cantilever.

The cantilever 137 is shown with a curvature or bend, which can represent the shape after sensing in one embodiment. As the cantilever 137 bends, the AWD responds by changing the frequency due to the non-linear elastic effects and density changes caused by the strain being transferred into the piezoelectric such as quartz. Thus in one embodiment, the structure forms a TSM device with the piezoelectric membrane as the diving board 135 such that if it bends, the device responds to the strain or flexure by changing its frequency.

For example, one mode of operation relates to static bending of the cantilever 137 due to gas adsorption or absorption by a film 160, wherein the frequency change will be related to the bending (curvature) of the thin piezoelectric membrane 135 due to film 160 elastic changes. The film 160 is shown on a portion of the cantilever 137. In other embodiments the film 160 can occupy the entire cantilever surface(s) or a small portion of the cantilever surface, all depending upon the design criteria. Multiple sensing films applied to a single cantilever 137 are also within the scope of the invention.

Additionally, because the resonator portion typically only responds to the strain coupled into the active acoustic area, it does not require a long cantilever. Rather, it only requires a cantilever 137 that is long enough to set up a consistent radius of curvature. If gas adsorption or absorption and resulting bending are linear with respect to gas concentration, frequency change of the AWD will be linear with respect to gas concentration over a wide range of strain. This particular design is well-suited for all kinds of sensing films (monolayer polymers, thin metal films, thin metal oxide films and others). Various biological and chemical responses can be measured using the present invention and the enhanced sensitivity provided therewith.

The cantilever can be any piezoelectric material such as quartz, as well as lithium niobate, lithium tantalate, langasite and its isomorphs, and any illustrative examples employing quartz are not to be deemed limiting.

There are additional applications in relation to liquid sensing and physical sensing that are also within the scope of the invention. For example, instead of using a sensing film on the cantilever, a magnetic film such as nickel can be disposed on the end of the cantilever. The device can be placed in the presence of a magnetic field such that the magnetic field would influence movement of the cantilever due to the magnetic coating. As an example, if you bias the device with a magnet in the presence of a gear tooth, it can measure speed. Such an example can be combined with an AWD in conjunction with a wireless transmitter thereby providing wireless magnetic sensing.

In one embodiment, the AWD is located proximate the fixed end of the cantilever with at least a portion of the cantilever having a sensing film for adsorption or absorption of a target gas. In another embodiment, such as a double-ended structure, the AWD is proximate the center of the cantilever. Multiple AWDs can be co-located about the cantilever. The placement of the AWD in the single-ended embodiment can be at the cantilever junction. In other embodiments, the AWD can be located along the cantilever length depending upon the design criteria.

For illustrative purposes, several examples of the cantilever shape/design are described herein. The examples include two basic types, namely rectangular cantilever and circular cantilever. There are further subsets with rectangular whole and rectangular half and circular whole and circular half. And there are variations for each with different length and angles. The present invention can be configured in a variety of shapes and sizes depending upon the design criteria. The shape can be symmetrical and can also be asymmetrical, wherein the asymmetrical design can be used to tailor for flexure effects. The use of rectangular and circular shapes is included to explain the teachings of the present invention and is not to be deemed limiting features. Other geometric shapes such as ovals, diamonds, triangles, and squares are all within the scope of the invention, as are free standing membranes of arbitrary outline.

In one embodiment the AWD is a small section of the cantilever. There can also be multiple AWDs about the cantilever depending upon the particular application and desired result.

Figure 5A:
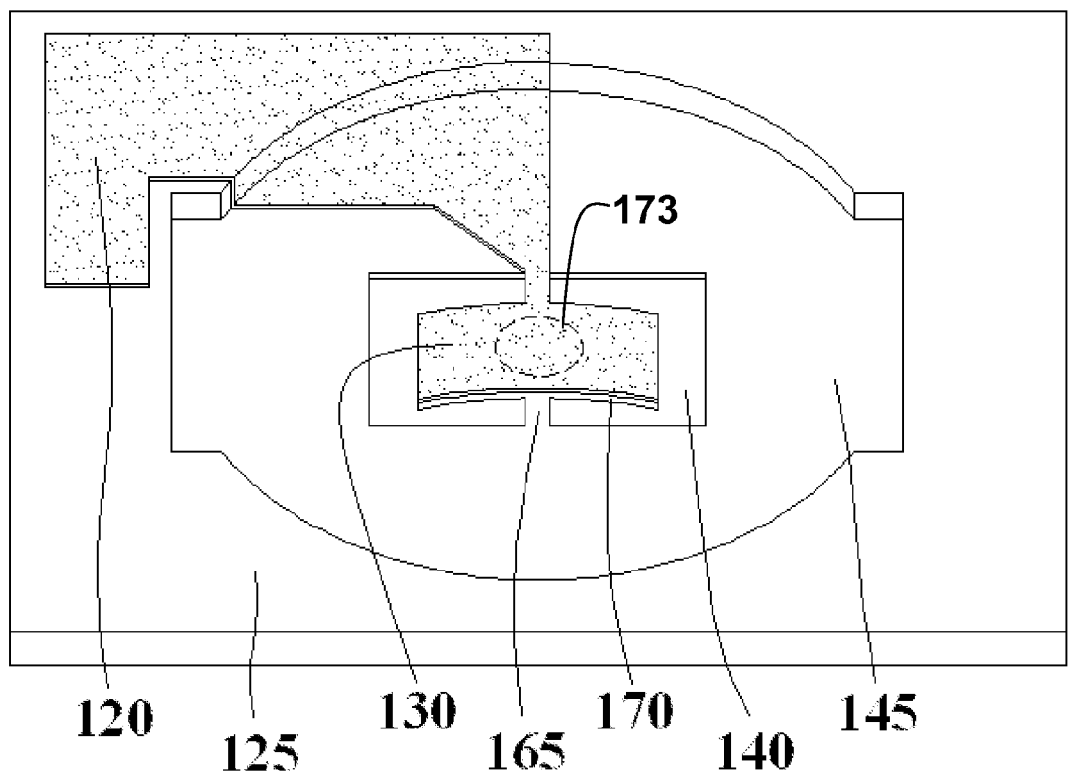
FIG. 5a is a top perspective view of a whole rectangle bulk acoustic wave (BAW) structure without a sensing film according to one embodiment of the present invention.
Figure 5B:
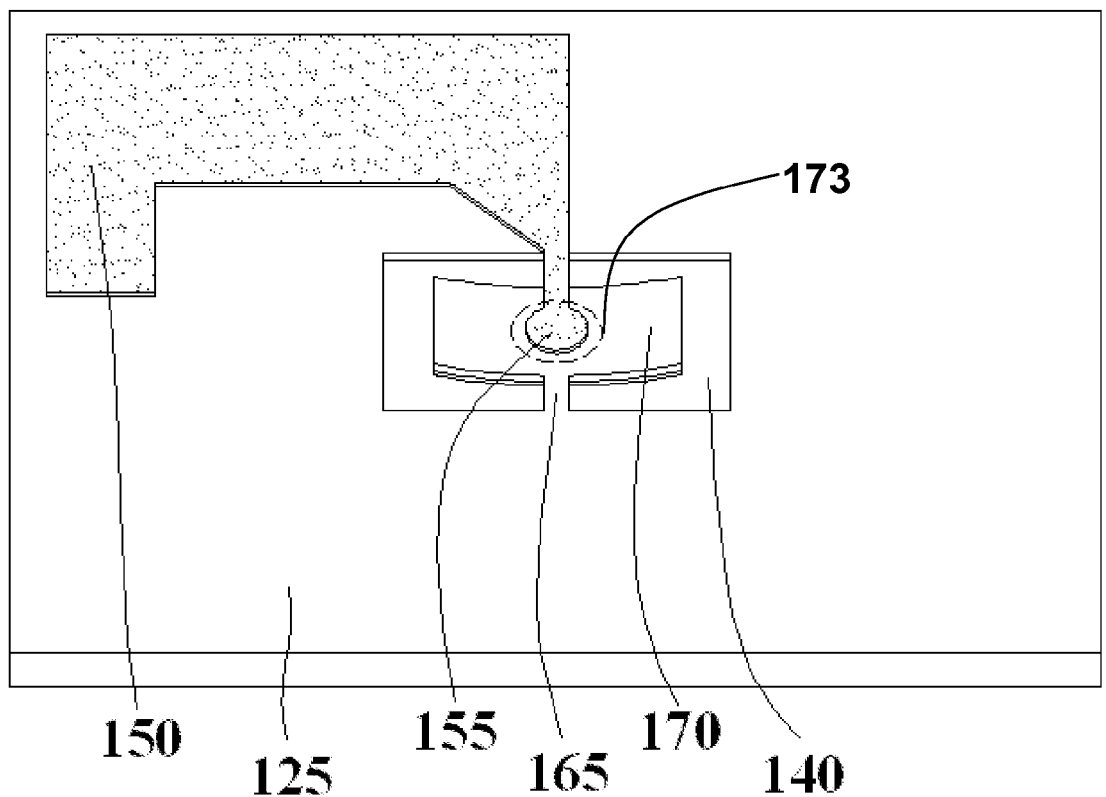
FIG. 5b is a bottom perspective view of the whole rectangle bulk acoustic wave (BAW) structure of FIG. 5a according to one embodiment of the present invention.
Figure 5C:
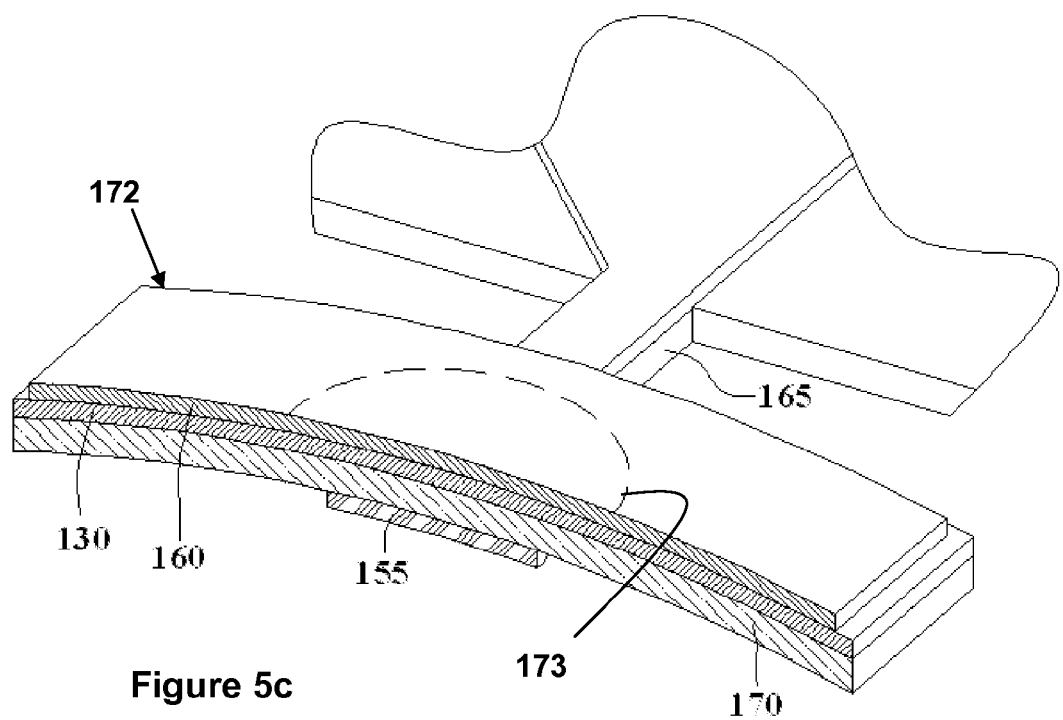
FIG. 5c shows a cut-away side perspective view of a whole rectangle bulk acoustic wave (BAW) structure according to one embodiment of the invention.

Referring to FIGS. 5a, 5b, 5c a whole rectangle structure is depicted which can be, for example, a TFE BAW structure. The device is electrically coupled as illustrated and known to those skilled in the art.

There is a piezoelectric substrate 125 with a ground electrical connection 120 disposed on one side which is electrically coupled to a ground electrode 130 and a positive electrical connection 150 disposed on the other side that is electrically coupled to a positive electrode 155. The positive electrode 155 and ground electrode 130 with the piezoelectric double-ended diving board 170 define the active acoustic region 173 for the AWD and the sensing film 160 is disposed on at least a portion of the ground electrode 130. In this embodiment, the cantilever 172 is coupled to the substrate 125 by a support tether 165 that holds the cantilever 172 in position. There may be more than a single support tether which can be oriented about the cantilever 172 depending upon the design criteria.

Figure 5D:
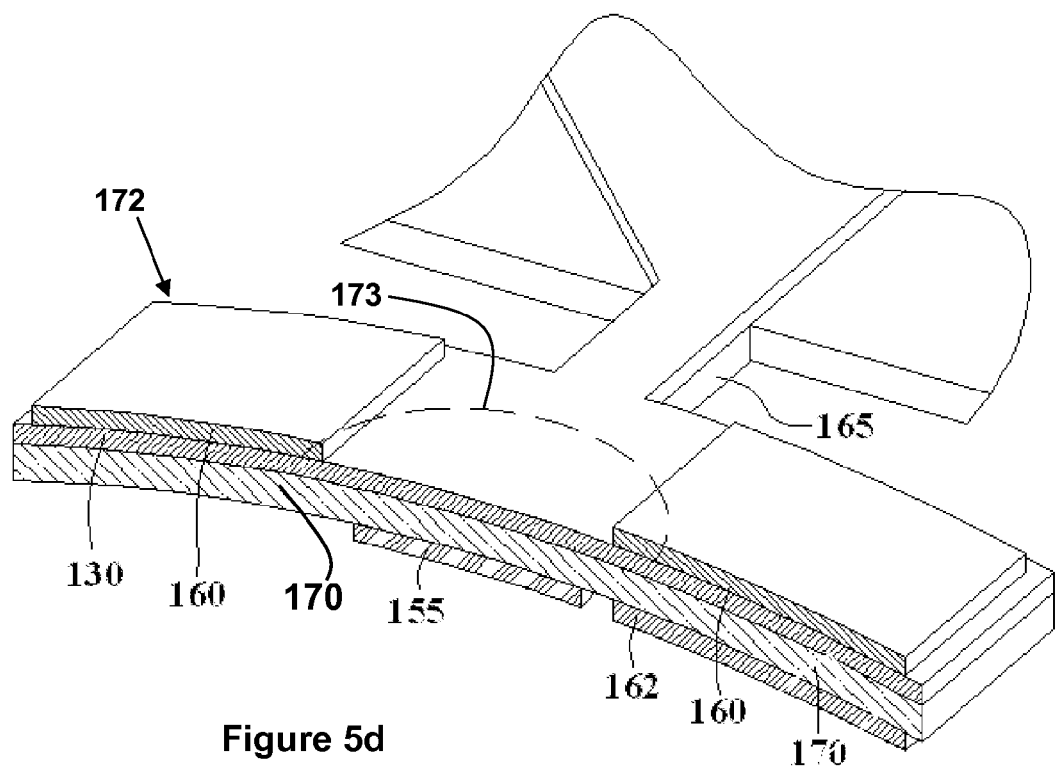
FIG. 5d shows a side perspective view of a whole rectangle bulk acoustic wave (BAW) structure with partial film coverage according to one embodiment of the invention.

Referring to FIG. 5d, a partially covered ground electrode 130 is illustrated with the upper sensing film 160 separated by an open area 167. This embodiment provides a mechanism to separate the detector from the viscoelastic loading of the sensing film 160 areas. As long as the strain due to flexure from the sensing film 160, 162 areas gets coupled to the AWD, the AWD provides a measurable frequency response. For example, the AWD can be isolated from the sensing film and still detect a gas as long as it can detect the strain within the cantilever 172. This embodiment may be useful in applications where the sensing films are viscoelastic and damp the acoustic mode. In another embodiment, the sensing film can be disposed upon the TSM area of the device and can be arranged such as in a striped pattern so that they are isolated and/or to columnate the induced strain and flexure along a specific axis of maximum sensitivity.

The cantilever 172 can have sensing films 160, 162 disposed on both sides of the cantilever either wholly or partially. By way of further example of the sensing film coverage, there are several options, namely only one side can be coated, both sides can be completely coated, one side can be completely coated while the other is partially coated, or both sides can be partially coated. According to certain embodiments, some asymmetry is required in order to induce strain as opposed to clamping stress. There can be two different types of sensing films that can sense two different target substances applied to the two surfaces, resulting in corresponding positive and negative shifts. For example, a fuel/air ratio can be sensed using a single sensor wherein one sensing film responds to oxygen and the other responds to combustibles. The placement of the sensing films on the opposing surfaces of the cantilever can also be used to increase sensitivity in certain applications. For example, disposing a sensing film introducing positive stress on the outer portion of the cantilever on one surface in the presence of combustibles and another film introducing negative stress on the inner portion of the cantilever on the other surface in the presence of oxygen or vice versa.

The rectangular designs of the cantilever obtain a fairly linear bending along the length of the cantilever, while the circular designs tend to have a "potato chip" like bending effect. As noted herein, other shapes are within the scope of the invention depending upon the design criteria and the application.

Figure 6A:
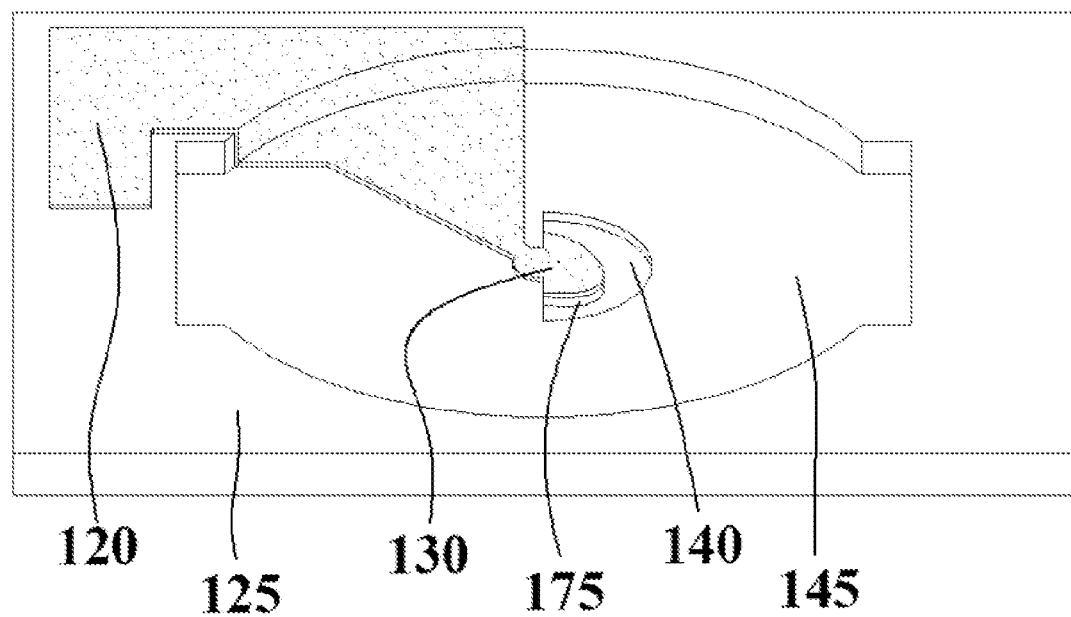
FIG. 6a is a top perspective view of a half circle bulk acoustic wave (BAW) structure without a sensing film according to one embodiment of the present invention.
Figure 6B:
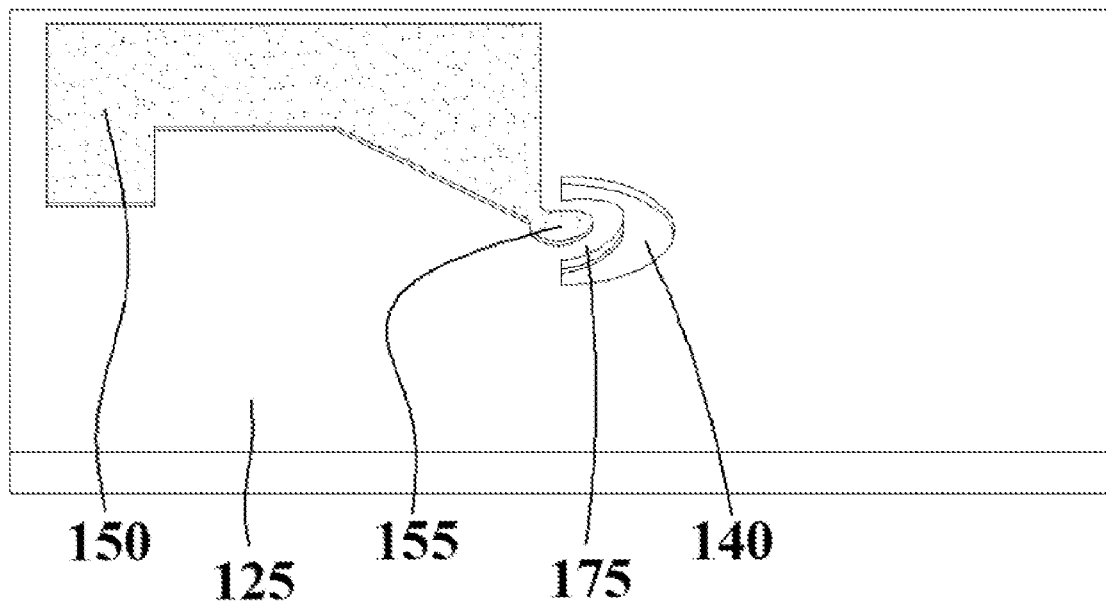
FIG. 6b is a bottom perspective view of the half circle bulk acoustic wave (BAW) structure of FIG. 6a according to one embodiment of the present invention.
Figure 6C:
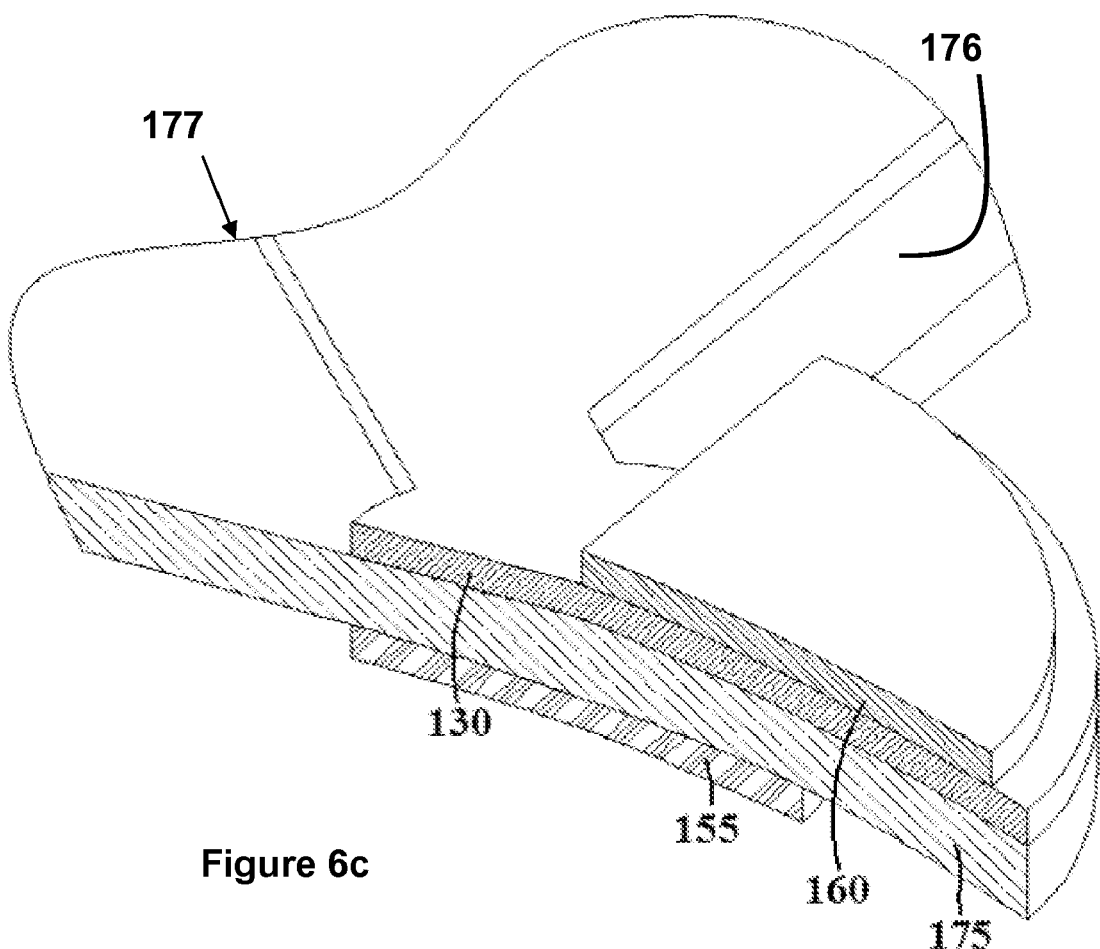
FIG. 6c shows a cut-away side perspective view of a half circle bulk acoustic wave (BAW) structure according to one embodiment of the invention.

Referring to FIGS. 6a, 6b and 6c, a half circle structure is depicted having a piezoelectric substrate 125 having a ground electrical connection 120 electrically coupled to the ground electrode 130 on one side and a positive electrical connection 150 electrically coupled to a positive electrode 155 on the other side. The cantilever 177 is formed by the etched relief 140 and has a fixed mount 176 anchoring the cantilever 177 to the substrate 120.

The active acoustic region is defined by the ground electrode 130, positive electrode 155 with the piezoelectric half-circular diving board 175 disposed therebetween. The sensing film 160 is disposed on at least a portion of the ground electrode 130.

Figure 14A:
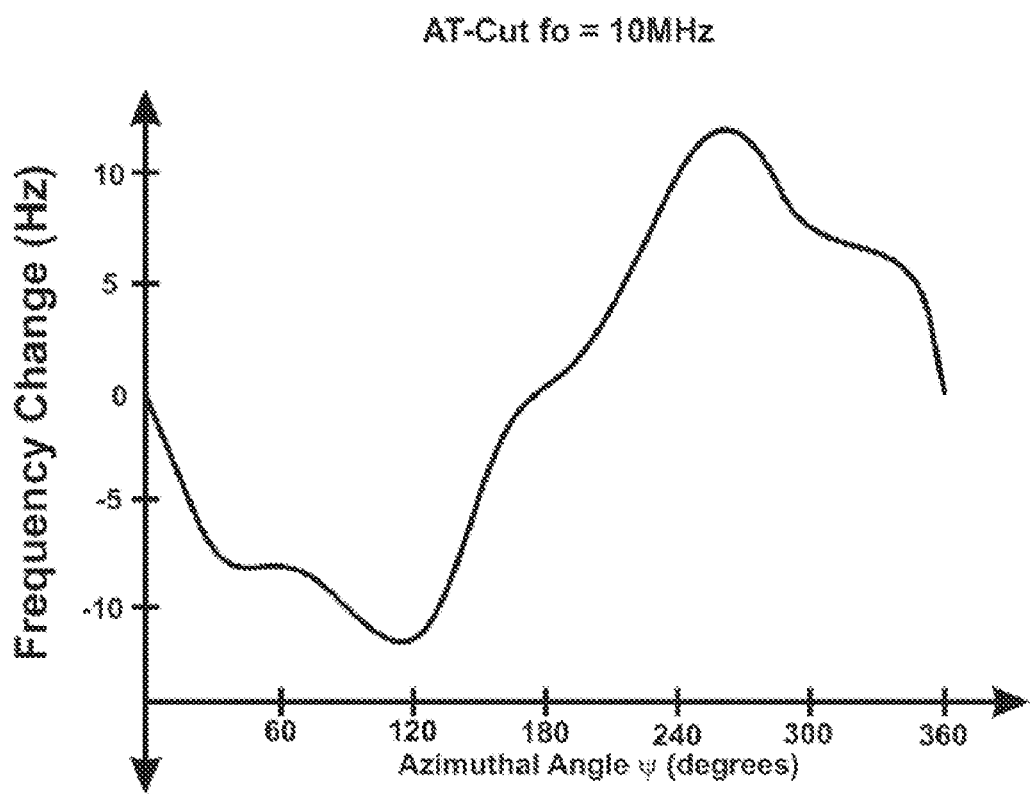
FIG. 14a is a graph of a published experimental AT-Cut Flexure response for 10 MHz thickness shear mode bulk acoustic wave (BAW) resonators.

Referring to FIG. 14a, there is a plot of frequency change versus azimuthal angle. In the semicircular and circular embodiments the flexure-frequency effect due to the strain of a bending member is a summation of the differential effects around the Ψ angle. In the rectangular versions, the direction of the strain is typically oriented in a single direction whereas the strain comes from other angles in the circular versions. This is further detailed herein.

Figure 7A:
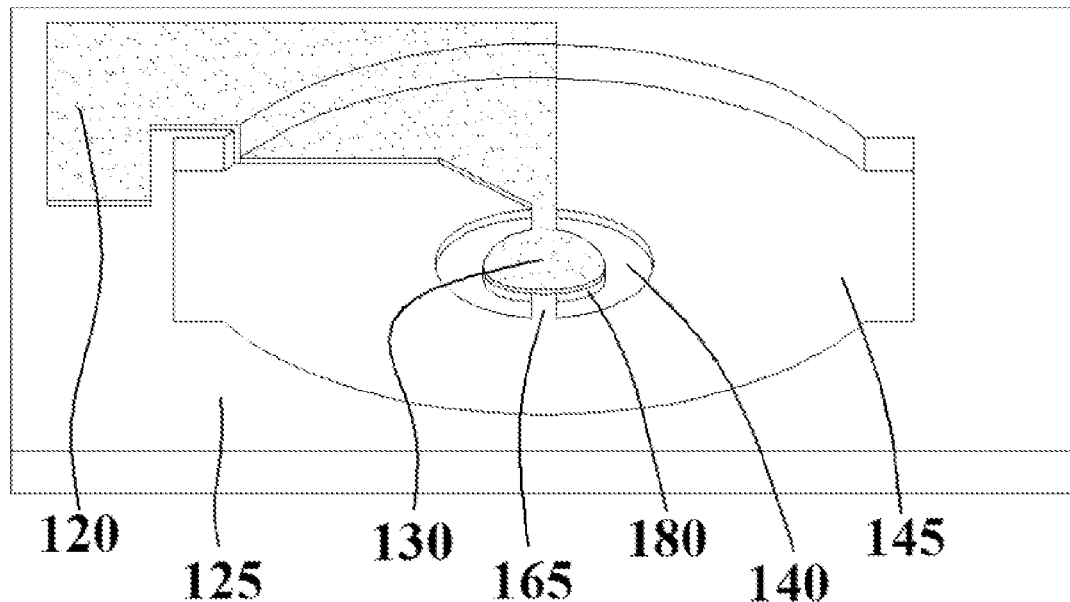
FIG. 7a is a top perspective view of a whole circle bulk acoustic wave (BAW) structure without a sensing film according to one embodiment of the present invention.
Figure 7B:
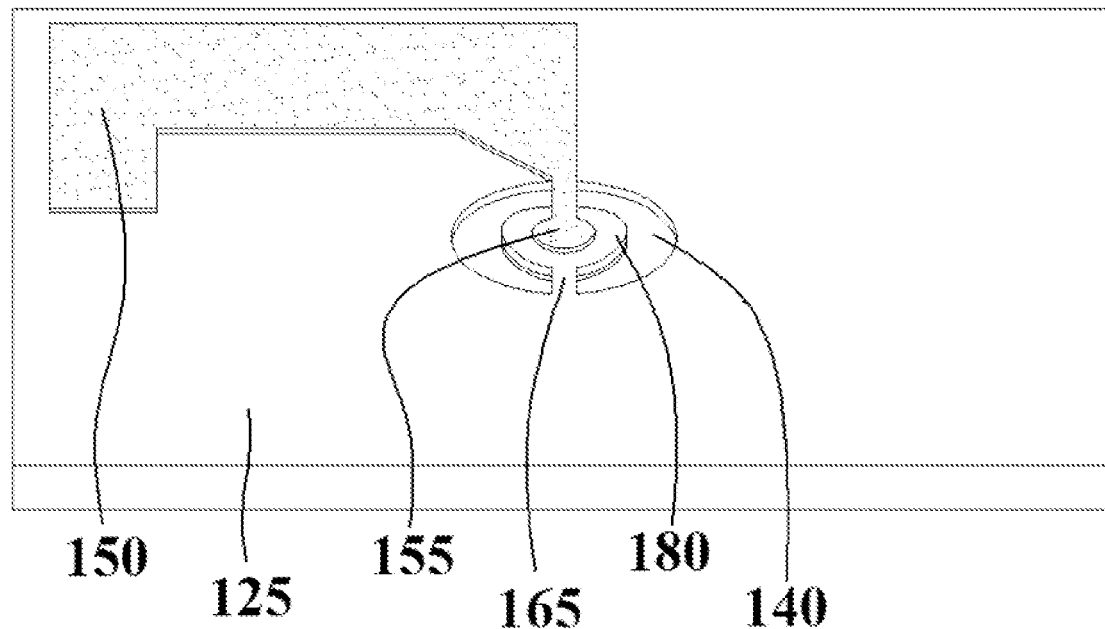
FIG. 7b is a bottom perspective view of the whole circle bulk acoustic wave (BAW) structure of FIG. 7a according to one embodiment of the present invention.
Figure 7C:
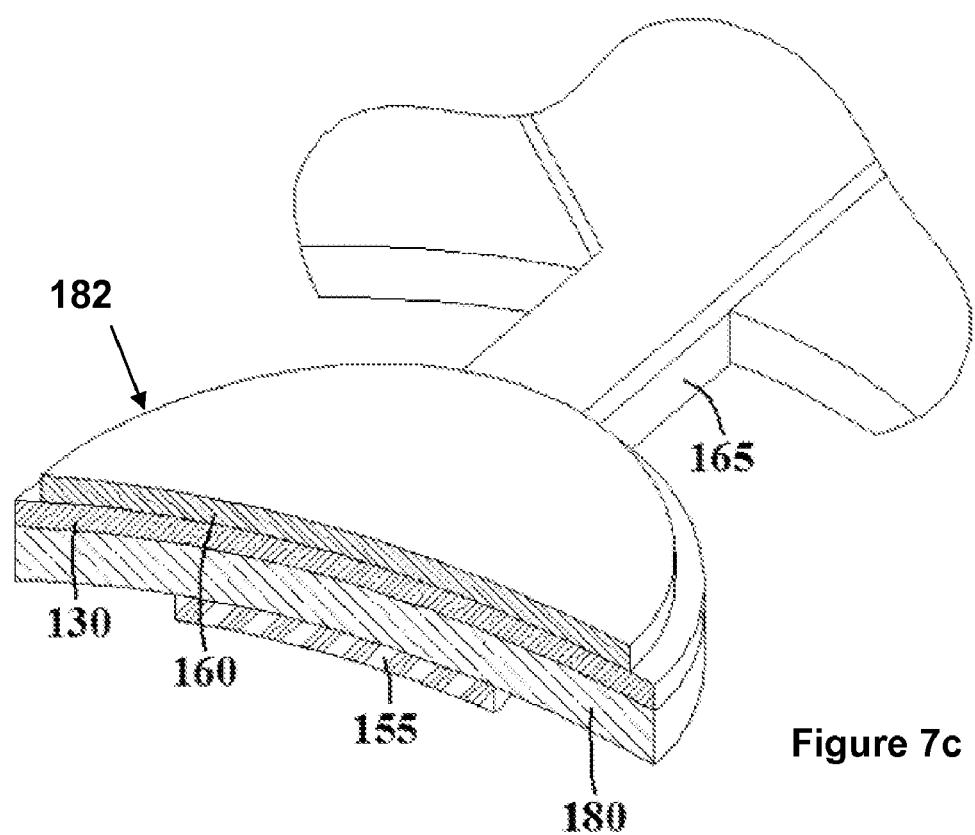
FIG. 7c shows a cut-away side perspective view of a whole circle bulk acoustic wave (BAW) structure according to one embodiment of the invention.

In the whole circle structure of FIGS. 7a, 7b, and 7c, the whole circle cantilever 182 is described. In this embodiment there is a single illustrated tether 165 however other angular orientations and additional tethers are within the scope of the embodiment. Once again the ground electrode 130 and the positive electrode 155 with the piezoelectric circular double-ended diving board 180 therebetween form the AWD that can be used in conjunction with full or partial coverage of the sensing film 160 upon the ground electrode 130 to influence the cantilever 182 and change the frequency response.

According to one embodiment, this circular design is affected by other angles and not just in the X direction. Thus for this tethered embodiment, the cantilever 180 wants to bend in the X direction and also in the Y direction but is somewhat prohibited which leads to some amount of incidental stresses from the mounting.

Figure 8A:
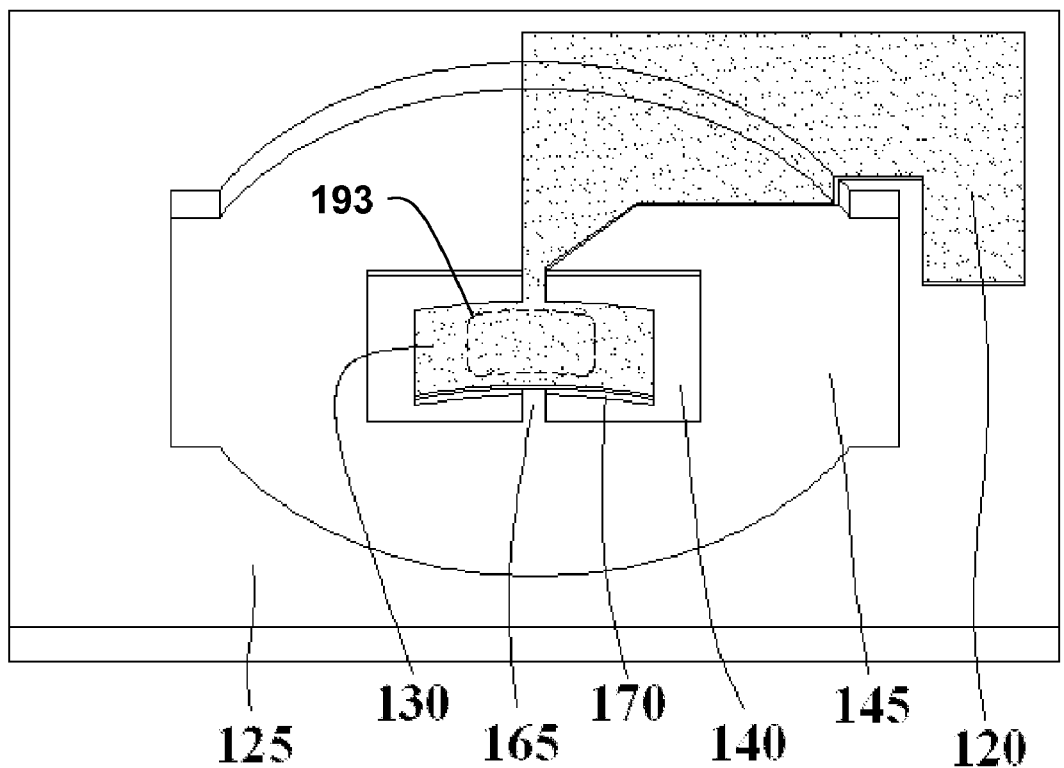
FIG. 8a is a top perspective view of a whole rectangle BAW monolithic crystal filter (MCF) structure without a sensing film according to another embodiment of the present invention.
Figure 8B:
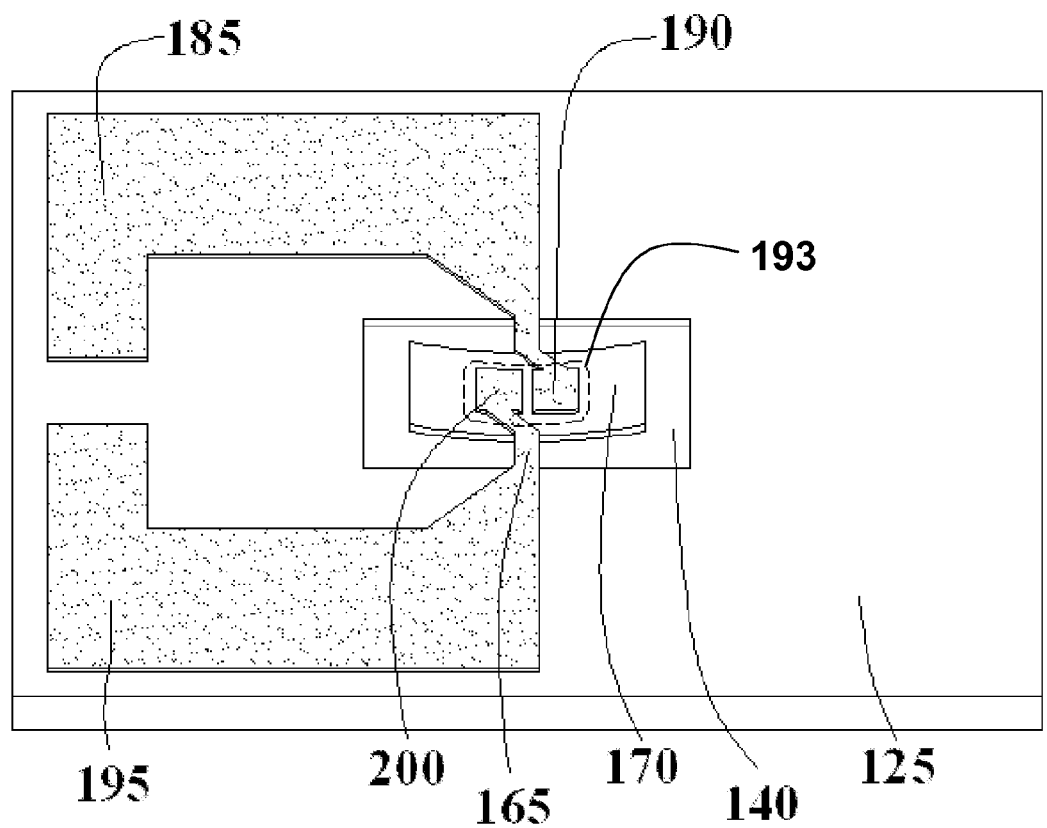
FIG. 8b is a bottom perspective view of the whole rectangle BAW monolithic crystal filter (MCF) structure of FIG. 8a according to another embodiment of the present invention.
Figure 8C:
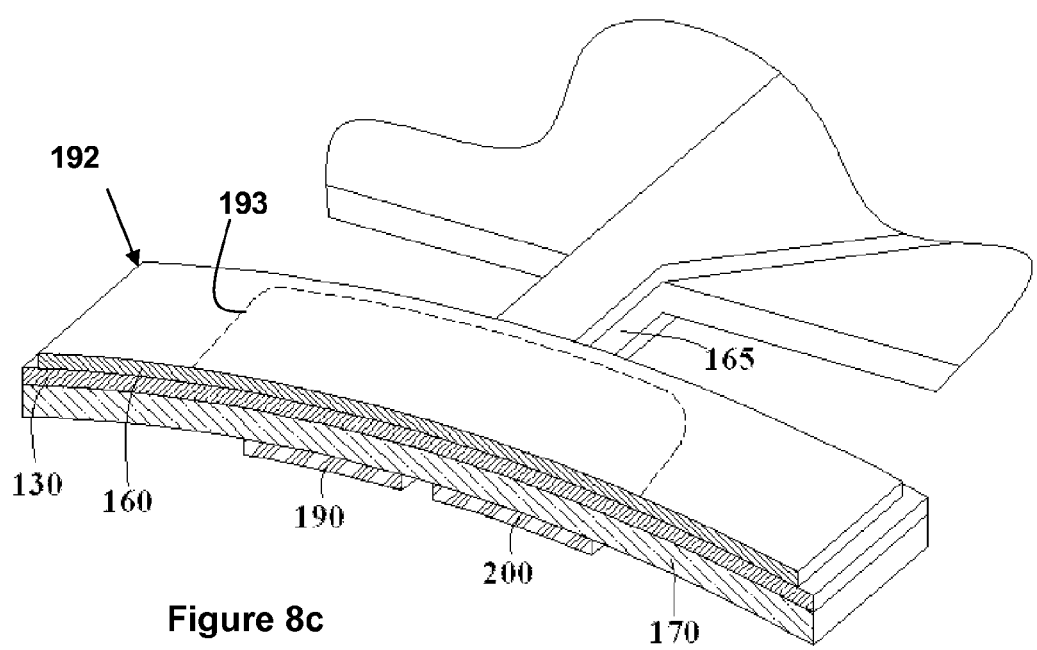
FIG. 8c shows a cut-away side perspective view of a whole rectangle BAW monolithic crystal filter (MCF) structure according to another embodiment of the invention.

Referring to FIGS. 8a, 8b, and 8c, a two port AWD is depicted, such as a monolithic crystal filter (MCF) device. On the piezoelectric substrate 125 there is a ground electrical connection 120 coupled to one or more ground electrodes 130 on one side of the substrate 125. On the other side of the substrate 125 are at least two positive electrodes.

In this embodiment, an input positive electrical connection 195 is disposed on the substrate 125 and electrically coupled to an input positive electrode 200 with the piezoelectric double-ended diving board 170 therebetween. This forms a first acoustic device, namely a TSM resonator, having an active acoustic region 193. There is also an output positive electrical connection 185 coupled to an output positive electrode 190 with the piezoelectric double-ended diving board 170 therebetween. This forms a second TSM resonator. When these resonators are sufficiently close so as to acoustically couple through shared acoustic energy they form a so-called acoustically coupled resonator filter or monolithic crystal filter (MCF) device.

One skilled in the art appreciates that the electrodes can be disposed in numerous other fashions and that the ground electrodes can be split into separate input and output ground electrodes.

In operation, as the cantilever 192 bends, it affects the coupling of the input to the output. The two port structure operates slightly different than a one port structure that only looks for the change of a single frequency. Employing the two port structure, one can look for frequency changes but, by virtue of the two-pole coupled resonator structure, there will be two frequencies wherein the two "pole" frequencies or resonances can be designed to coincide or to be separated for various applications.

According to one embodiment the design can implement different levels of coupling between the electrodes, for situations such as overcoupled, undercoupled, and critically coupled operation. The determination of whether the device operates in a particular mode depends upon whether the two electrodes are close enough for the required level of coupling effects. Wide separations and low couplings are in the so-called under-coupled operating range and are characterized by excessive insertion loss due to the poor signal coupling. Designs wherein the electrode spacing, and therefore the coupling there-between, is at a critical value will result in both electronic resonances being at the same frequency, yielding a Butterworth filter function. As the electrodes are placed in closer proximity the reactance of one resonator affects the other and the filter function presents two peaks in a Chebycheff filter function. The frequency spacing between these two frequencies is related to the degree of over-coupling of the electrodes. For background reference, U.S. Pat. No. 6,033,852 describes certain embodiments.

According to one embodiment, the bending of the cantilever affects the region between the resonators and therefore affects the coupling aspects. In other words, the device could be operating in or near a critically coupled mode and a change in the cantilever might shift the frequencies apart such that it becomes over-coupled. Similarly the device could be operating at or just below critical coupling and an induced decrease in coupling would result in an increased insertion loss. It is also possible to create a common-mode shift of both frequencies in an over-coupled structure.

Figure 9A:
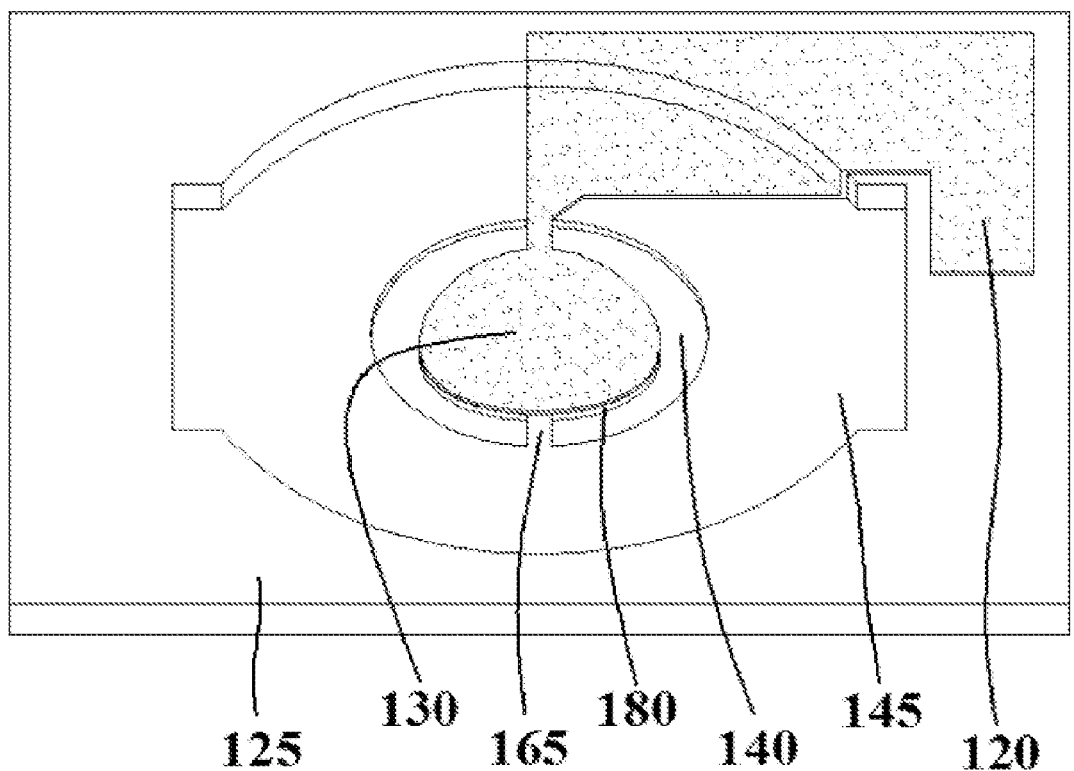
FIG. 9a is a top perspective view of a whole circle BAW monolithic crystal filter (MCF) structure without a sensing film according to another embodiment of the present invention.
Figure 9B:
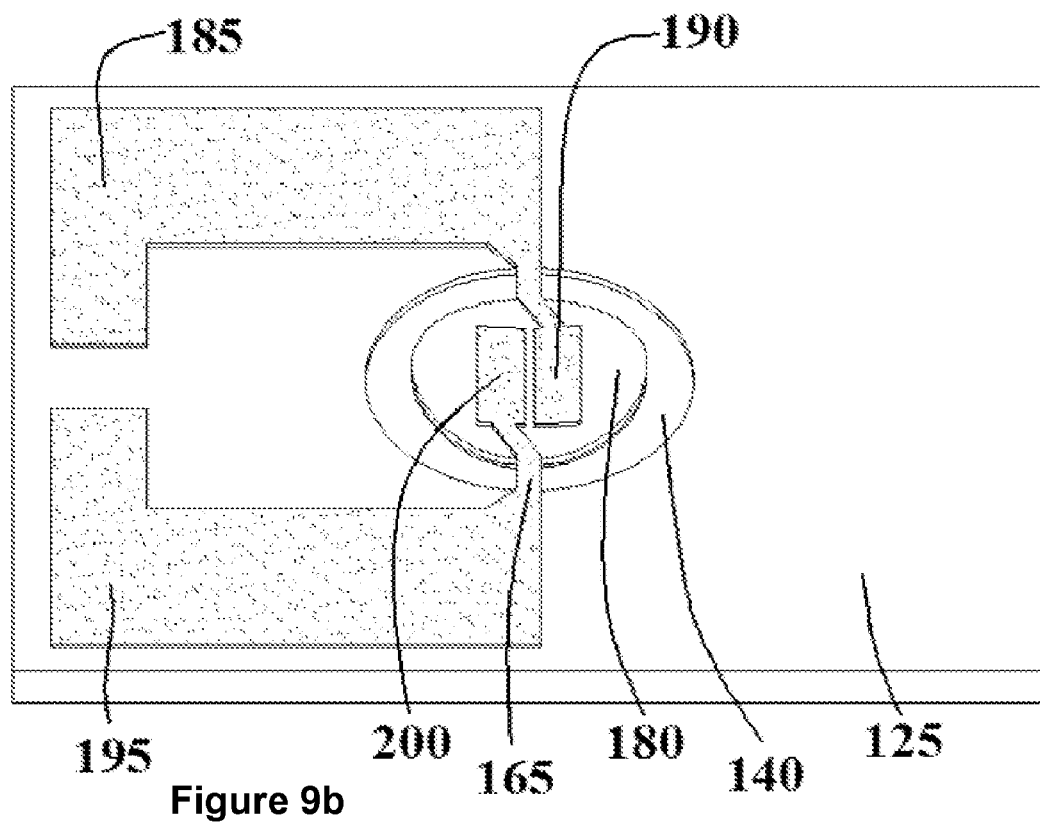
FIG. 9b is a bottom perspective view of the whole circle BAW monolithic crystal filter (MCF) structure of FIG. 9a according to another embodiment of the present invention.
Figure 9C:
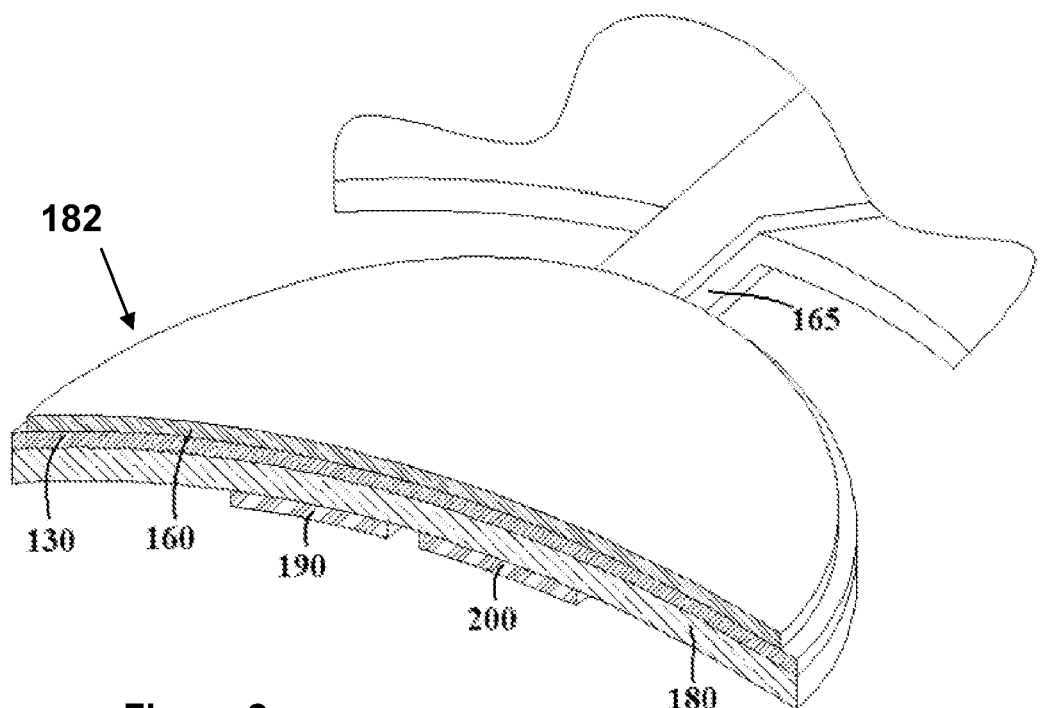
FIG. 9c shows a cut-away side perspective view of a whole rectangle BAW monolithic crystal filter (MCF) structure according to another embodiment of the invention.
Figure 10A:
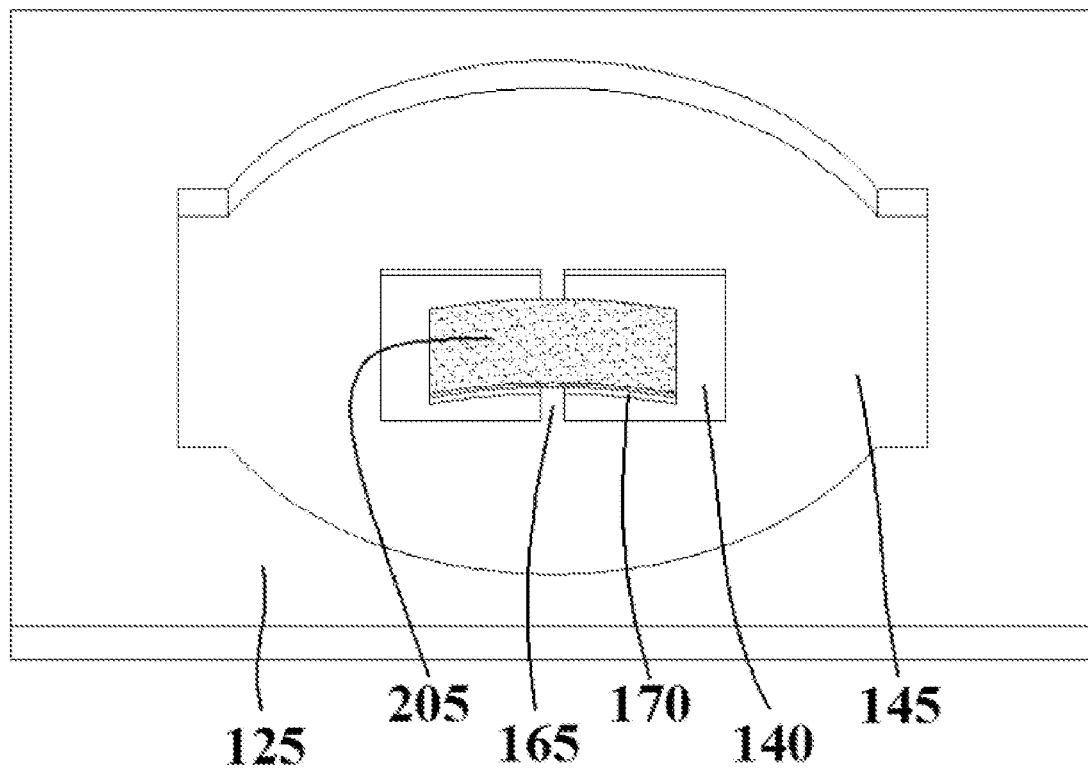
FIG. 10a is a top perspective view of a whole rectangle surface generated acoustic wave (SGAW) structure without a sensing film according to one embodiment of the present invention.
Figure 10B:
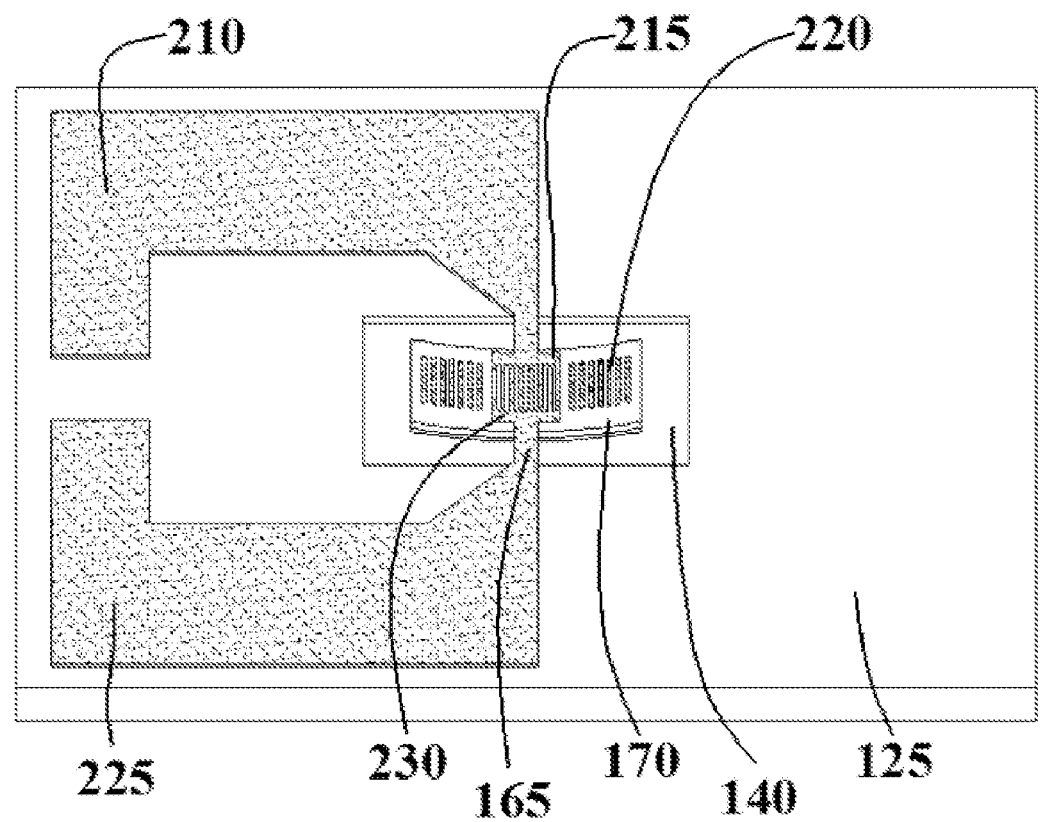
FIG. 10b is a bottom perspective view of the whole rectangle surface generated acoustic wave (SGAW) structure of FIG. 10a according to one embodiment of the present invention.
Figure 10C:
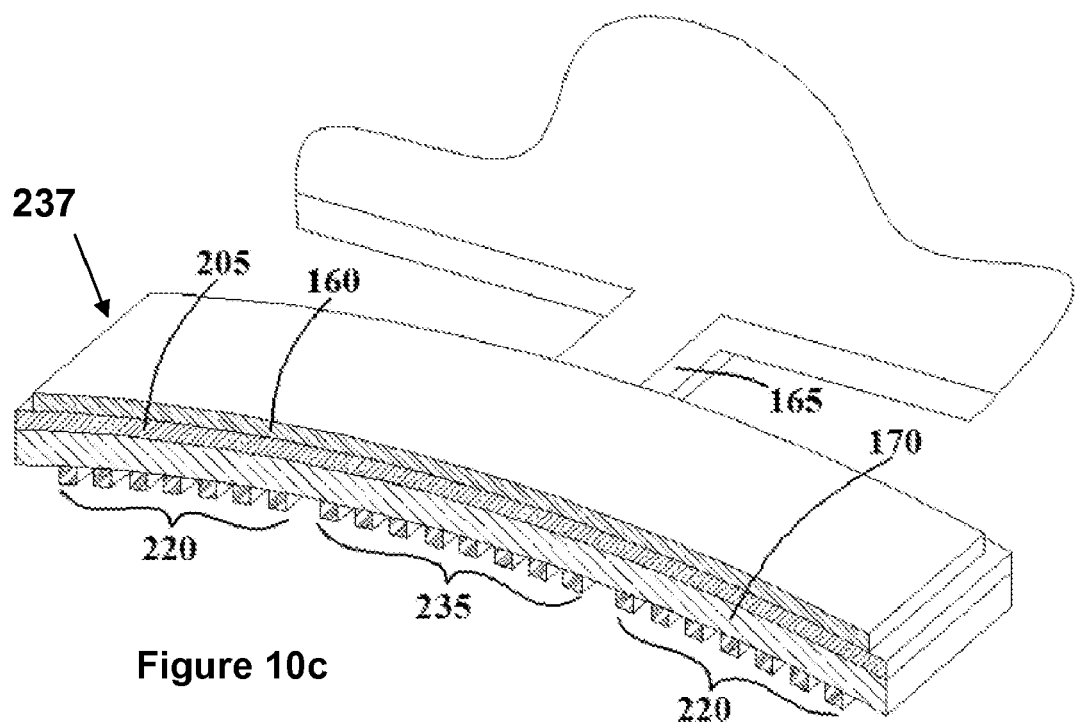
FIG. 10c shows a cut-away side perspective view of a whole rectangle surface generated acoustic wave (SGAW) structure according to one embodiment of the invention.
Figure 10D:
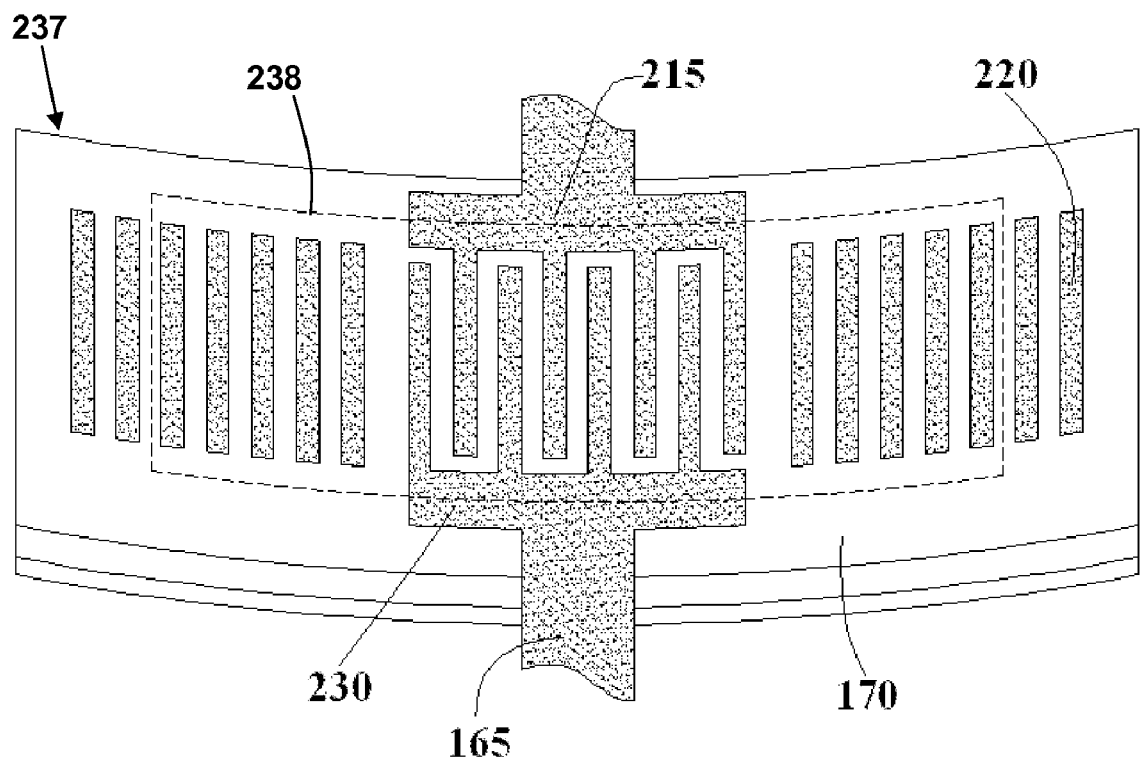
FIG. 10d shows is an enlarged perspective view of the whole rectangle surface generated acoustic wave (SGAW) structure of FIG. 10a according to one embodiment of the present invention.

Referring to FIG. 9a, a whole circle MCF structure is depicted wherein the two port device provides for two resonators and the coupling effects allow for certain design criteria. As previously noted, the piezoelectric circular double-ended diving board 180 is sandwiched between one or more ground electrodes 130 on one side and a pair of positive electrodes 190, 200 on the other side, thereby forming two TSM resonators side by side to each other. There is an input positive electrode 200 forming an input TSM resonator and an output positive electrode 190 forming an output TSM resonator. The sufficient proximity of these resonators causes coupling effects and integrates them into an MCF device. As previously noted, the cantilever structure 182 is coupled to the substrate by at least one tether 165.

Referring to FIGS. 10a, 10b, 10c and 10d, an SGAW structure on a cantilever is depicted. According to one embodiment, the surface-launched AWDs employ some form of surface displacement mediums in order to detect and quantify numerous measurands by means of perturbations induced in the electrical and mechanical properties of the devices by those measurands.

Referring again to FIGS. 10a, 10b, 10c and 10d, the rectangular cantilever 237 has a metallized back surface 205 which is typically floating although it can be considered a ground plane in certain embodiments. For example, the metallized back surface 205 can be 'grounded' in certain ways such as with uniphase transducers.

There is a positive one-port electrical connection 210 coupled to a positive one-port bus bar 215. On the other side there is a negative one-port electrical connection 225 that is coupled to a negative one-port bus bar 230. One or more surface gratings 220 are optionally disposed on the cantilever 237 wherein an interdigital transducer (IDT) 235 is placed in between the two sets of surface gratings 220. The reflective gratings 220 do not need to have the same number of fingers or the same grating period as the IDT 235. The one port IDT 235 serves as both the input IDT and the output IDT with the end gratings 220 providing the reflections. The AWD with the respective active acoustic region 238 is formed from the metallized surface 205, the piezoelectric section 170, and the IDT 235. The active acoustic region 238 of the AWD resides within the edges of the cantilever 237 and according to one embodiment the region lies within the bounds of the end gratings 220.

Other embodiments include dispersive, non-dispersive, resonant, and delay line structures. For example, a two port transducer such as shown in FIG. 2a which includes an input transducer and an output transducer is within the scope of the invention for a SGAW cantilever, either in the delay line structure shown, or in various well-known two-port single and multi-pole resonator structures using reflective gratings 220. On the surface transducer side, the acoustic waves are generated and measured using interdigital transducers (IDTs) disposed on the piezoelectric diving board 170. A SAW implementation may have an input IDT and an output IDT with a delay line therebetween. A STW implementation may have an input and out transducer with a metal trapping grating, either as the IDT or there-between. A Love Mode device can use thin film trapping layers. A shear-horizontal APM may include input and output transducers interacting with surface displacements on both surface of the plate for sensing.

According to one embodiment the piezoelectric diving board 237 can be constructed including materials such as quartz and its isomorphs, lithium niobate, lithium tantalate, langasite and its isomorphs, and the like, wherein an electric potential is converted into a mechanical energy and vice versa. The specific geometry of the substrate and interdigital transducers and the type and crystallographic orientation of the substrate material determine the spectrum of waves that are excited and measured.

Of particular interest are polymer films disposed on the cantilever surface opposite the SGAW transducer. Such films will not damp the SGAW but will couple film stress into cantilever flexure; altering the SGAW properties.

Figure 11A:
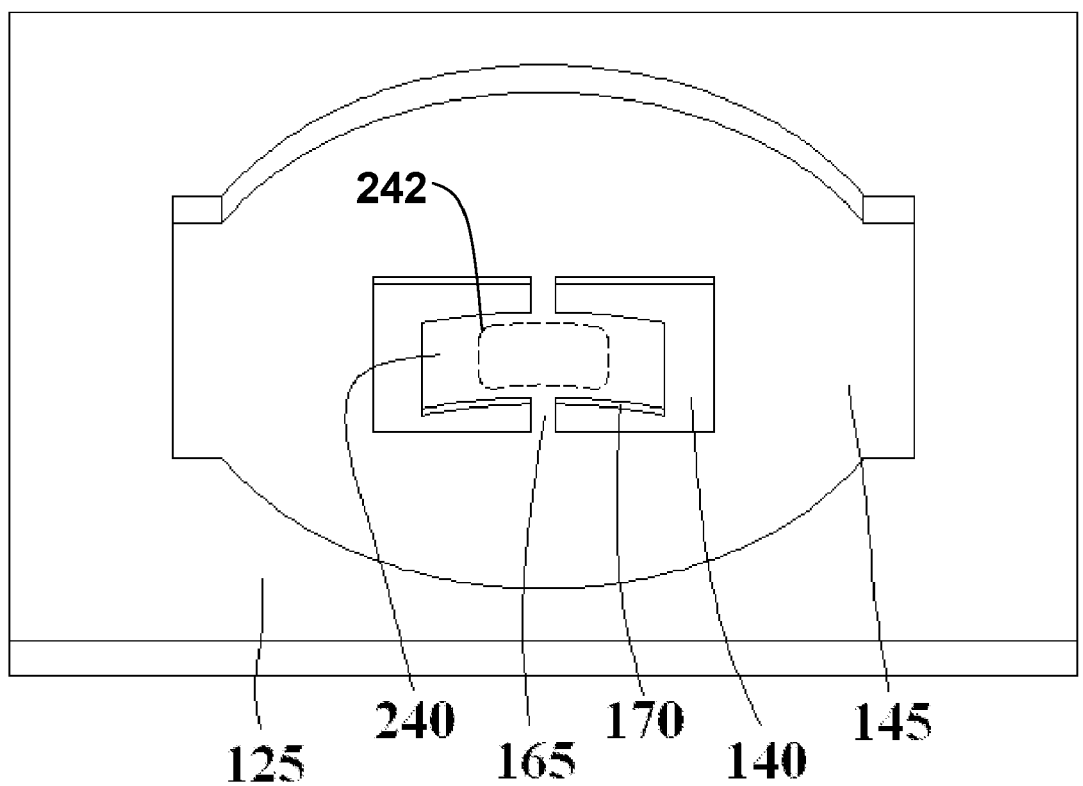
FIG. 11a is a top perspective view of a whole rectangle BAW lateral-field excitation (LFE) structure without a sensing film according to one embodiment of the present invention.
Figure 11B:
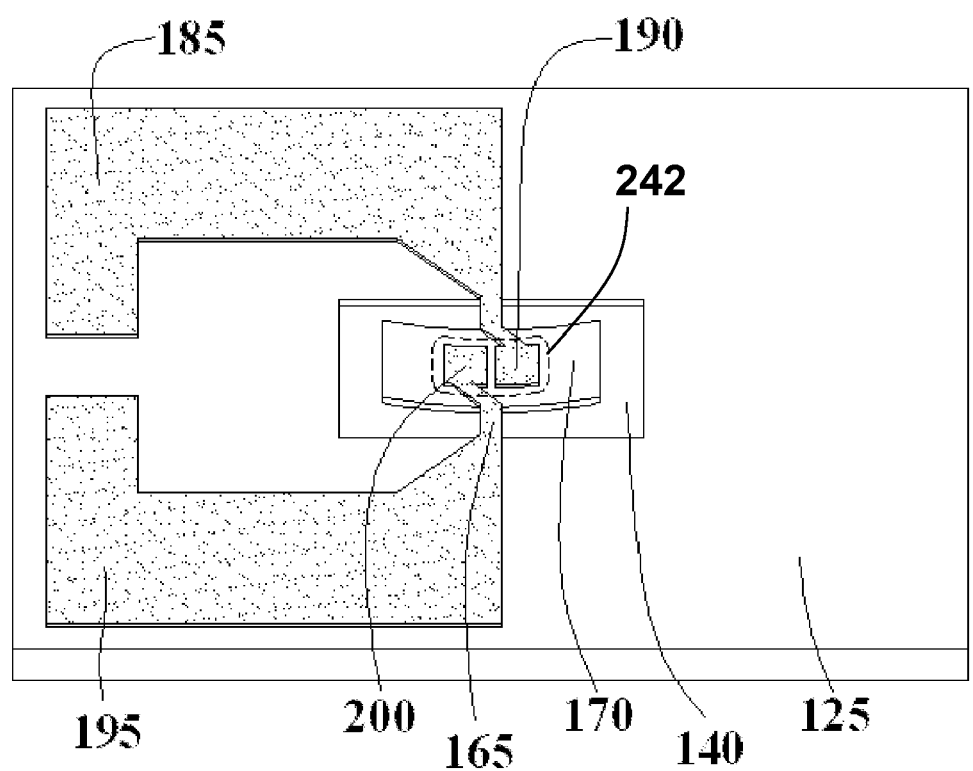
FIG. 11b is a bottom perspective view of the whole rectangle BAW lateral-field excitation (LFE) structure of FIG. 11a according to one embodiment of the present invention.
Figure 11C:
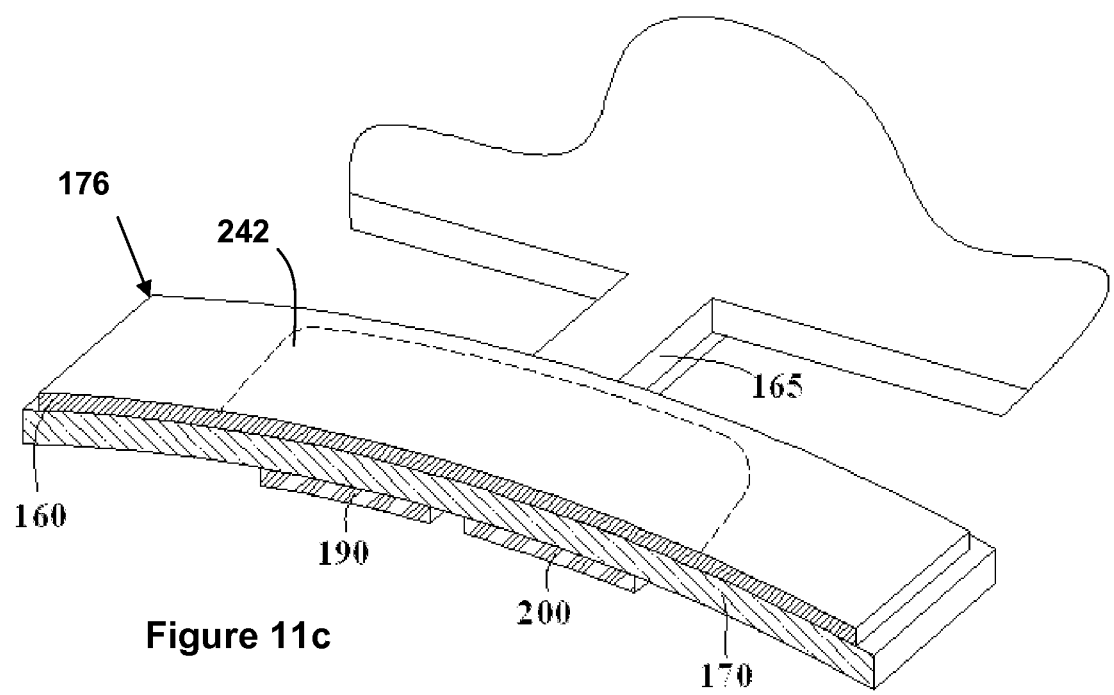
FIG. 11c shows a cut-away side perspective view of a whole rectangle BAW lateral-field excitation (LFE) structure according to one embodiment of the invention.

Referring to FIGS. 11a, 11b, and 11c, a whole rectangle lateral field excitation (LFE) structure is depicted. In this particular embodiment, the cantilever 176 has a bare surface 240. The sensing film 160 is disposed on the double-ended diving board 170. On the opposing side, there are the two electrodes, namely an input positive electrode 200 and an output positive electrode 190. The active acoustic region 242 for the AWD is formed from the piezoelectric section 170, the electrodes 190, 200. This embodiment is not subject to thickness field excitation (TFE) which typically requires that there be electrodes on top and bottom so that the fields go through the device. Instead, this embodiment is subject to lateral field excitation (LFE) in which there are only electrodes on one side and the fields traverse the device laterally between the two electrodes 190, 200 on the same side.

Figure 12A:
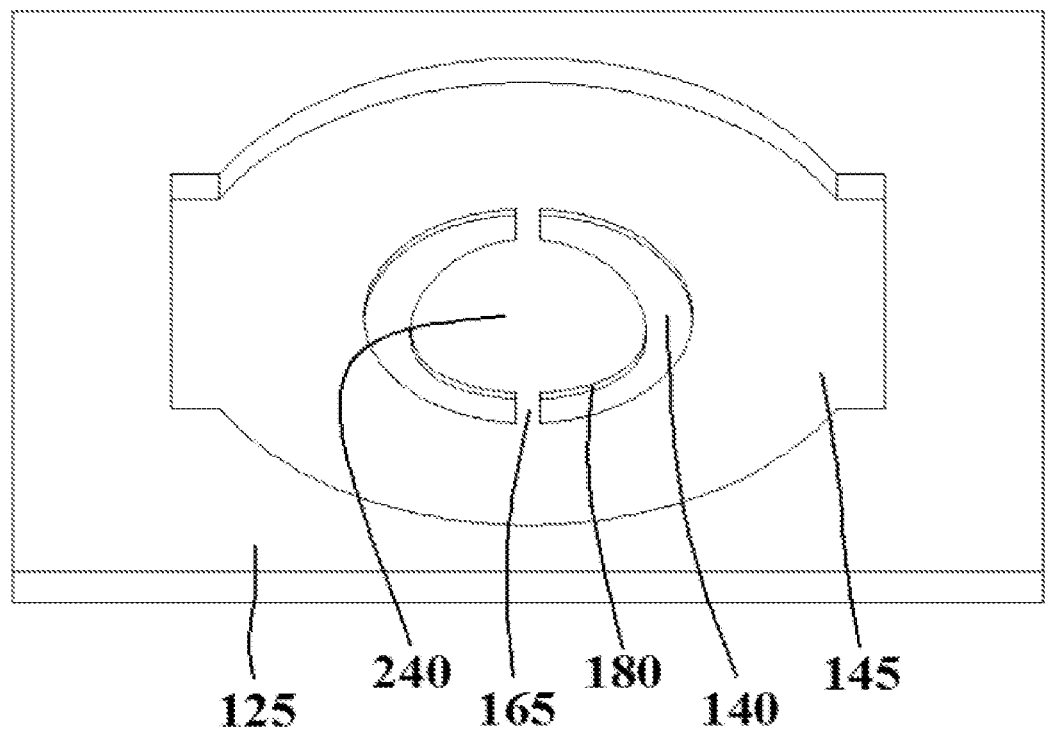
FIG. 12a is a top perspective view of a whole circle BAW lateral-field excitation (LFE) structure without a sensing film according to one embodiment of the present invention.
Figure 12B:
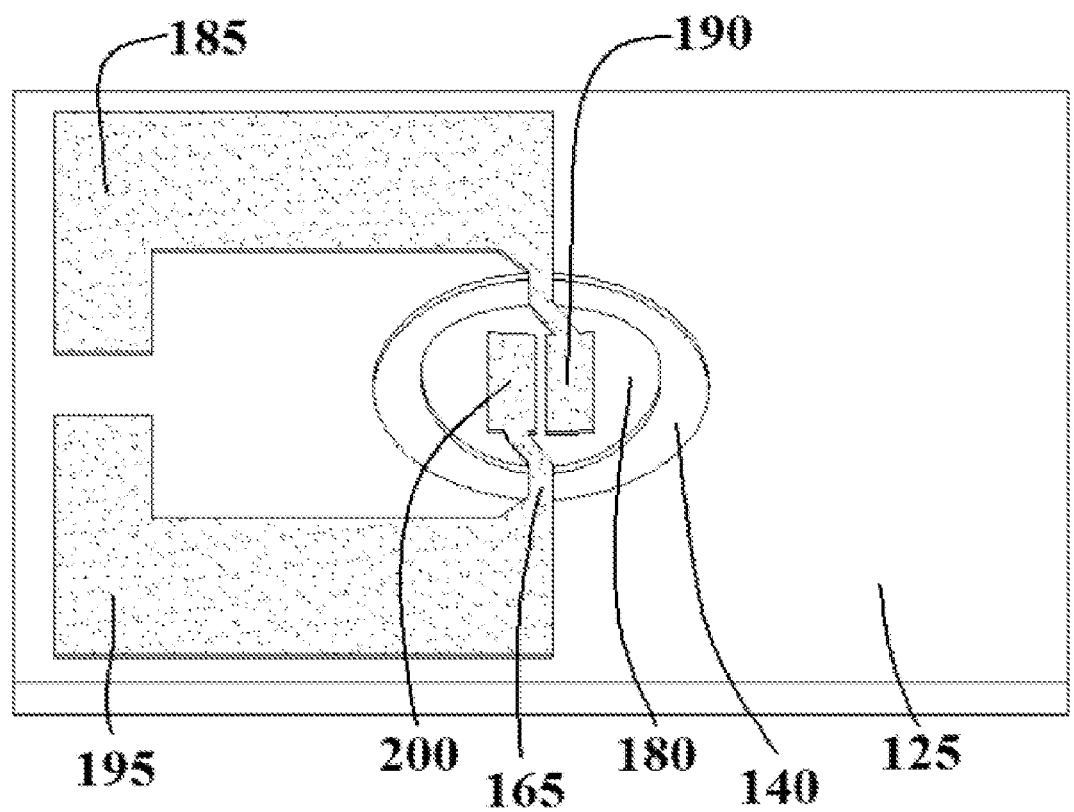
FIG. 12b is a bottom perspective view of the whole circle BAW lateral-field excitation (LFE) structure of FIG. 12a according to one embodiment of the present invention.
Figure 12C:
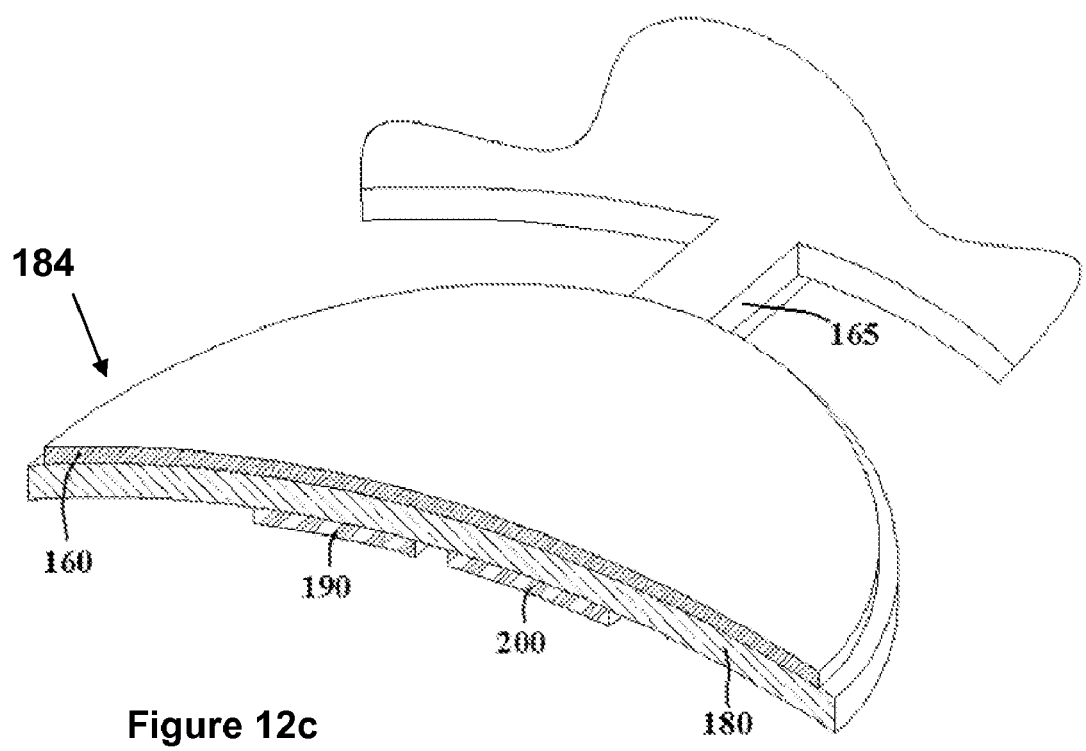
FIG. 12c shows a cut-away side perspective view of a whole circle BAW lateral-field excitation (LFE) structure according to one embodiment of the invention

FIGS. 12a, 12b and 12c show another lateral field excitation structure for the whole circle. In these figures, the cantilever 184 is devoid of the ground electrode and has a bare surface with the exception of the sensing film 160 that is disposed upon the circular double ended diving board 180. On the opposing side, there is an input positive electrode 200 that is coupled to the corresponding input positive electrical connection 195 and an output positive electrode 190 coupled to a corresponding output positive electrical connection 185. The lateral filed excitation (LFE) occurs between the two electrodes 190, 200.

Figure 13A:
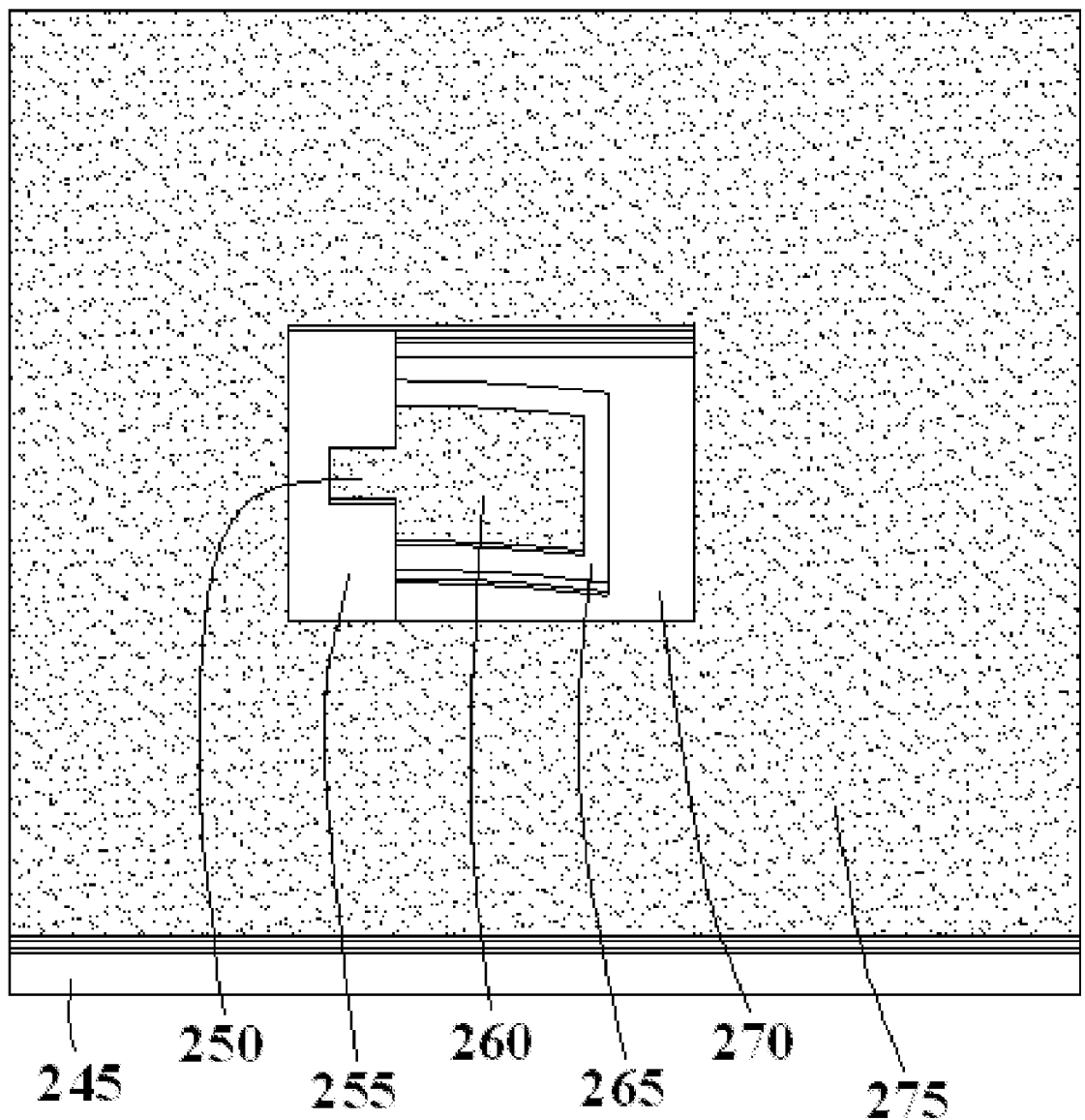
FIG. 13a is a top perspective view of a rectangular BAW film bulk acoustic resonator (FBAR) structure without a sensing film according to one embodiment of the present invention.
Figure 13B:
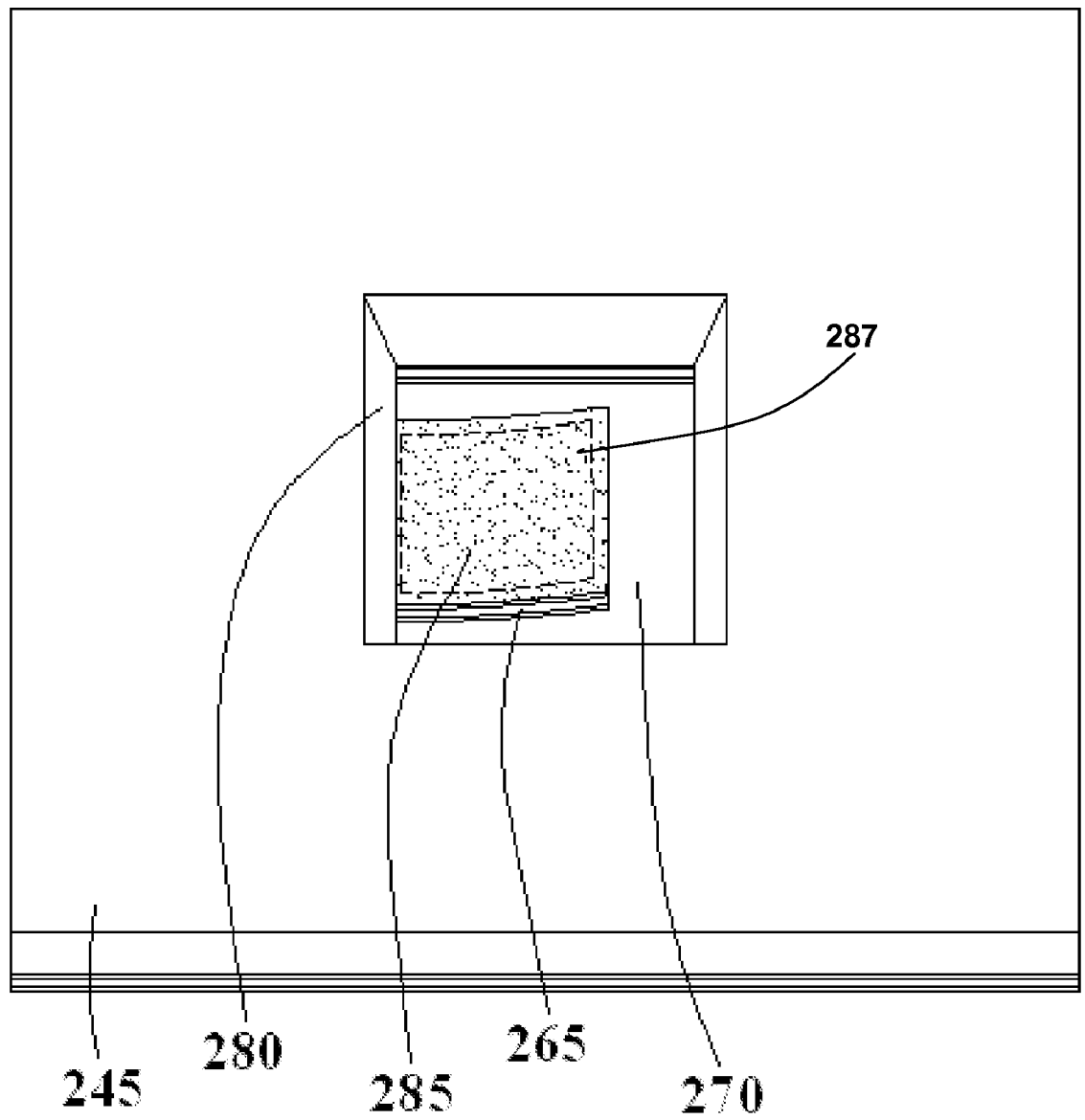
FIG. 13b is a bottom perspective view of the rectangular BAW film bulk acoustic resonator (FBAR) structure of FIG. 13a according to one embodiment of the present invention.
Figure 13C:
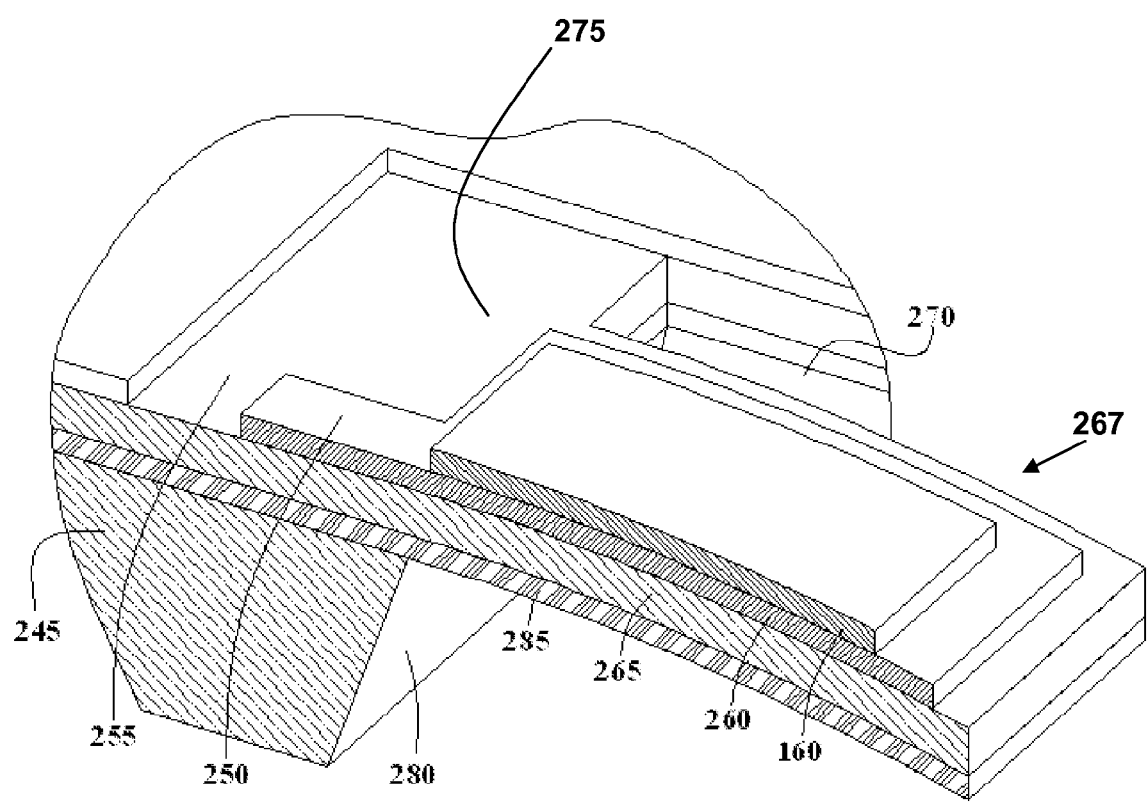
FIG. 13c shows a cut-away side perspective view of a rectangular BAW film bulk acoustic resonator (FBAR) structure according to one embodiment of the invention.

Referring to FIGS. 13a, 13b, and 13c, a film bulk acoustic resonator (FBAR) is shown. In this embodiment, the piezoelectric diving board 265 or other structure and surrounding areas are covered by ground electrode 285 and optionally the ground contact 275. The cantilever 267 and at least a portion of the surrounding ground electrode 285 is further covered by epitaxial piezoelectric layer 255. The piezoelectric layer 255 then supports a positive electrical connection 250 and a positive electrode 260 which defines the FBAR device having acoustic energy confined to a portion of the cantilever 267. Alternately the piezoelectric layer is uniformly disposed onto the uniform ground plane and the ground electrode 285 is electrically coupled to a ground connection 275, disposed onto the piezoelectric, using vias (not shown) through the thin film piezoelectric layer 255. The active acoustic region 287 of the AWD resides on a portion of the cantilever 267. The cantilever relief 270 defines the perimeter of the rectangular cantilever structure 267 and the FBAR piezoelectric layer 265 separates the positive electrode 260 and the ground electrode 285. A base substrate pocket 280 allows the cantilever structure to be free-standing. Optionally the cantilever can consist of the FBAR supported on a residual silicon layer.

The cantilever structure 267 of FIG. 13c shows the ground electrode 285 disposed on a portion of the base 245 and extends outwards from the base over the pocket 280. The FBAR rectangular diving board 265 is disposed on the ground electrode 285 and a portion of a positive electrical connection 250 is disposed on a section of the piezoelectric 255, which also supports the positive electrode 260. The sensing film 160 is either disposed on the ground electrode 285 or on at least a portion of the surface of the cantilever 265 supporting the positive electrode 260.

The FBAR can operate with Thickness Field Excitation (TFE) which uses a z-directed electric field to generate z-propagating longitudinal or compressive wave. In a Lateral Field Excitation (LFE) FBAR, the applied electric field is in y-direction, and the shear acoustic wave (excited by the lateral electric field) propagates in z-direction. The defining difference between the FBAR of the present invention and traditional MEMS cantilevers is that the resonator is a distinct trapped energy resonator located within the geometrical extent of the cantilever, whereas in the prior art the entire cantilever is also the resonator.

Referring to the FIG. 14a, it has been demonstrated that there is an optimal frequency change as shown in the frequency response curve. Some of the embodiments herein include orienting the cantilever for maximum sensitivity. Referring to "*A Comparison of the Effects of Bending Moments on the Vibrations of AT and SC (or TTC) Cuts of Quartz*" by E. D. Fletcher and A. J. Douglas paper, incorporated by reference herein, there are optimal directions for sensitivity to flexure. Thus, the cantilever device can be oriented along a certain azimuthal direction.

Figure 14B:
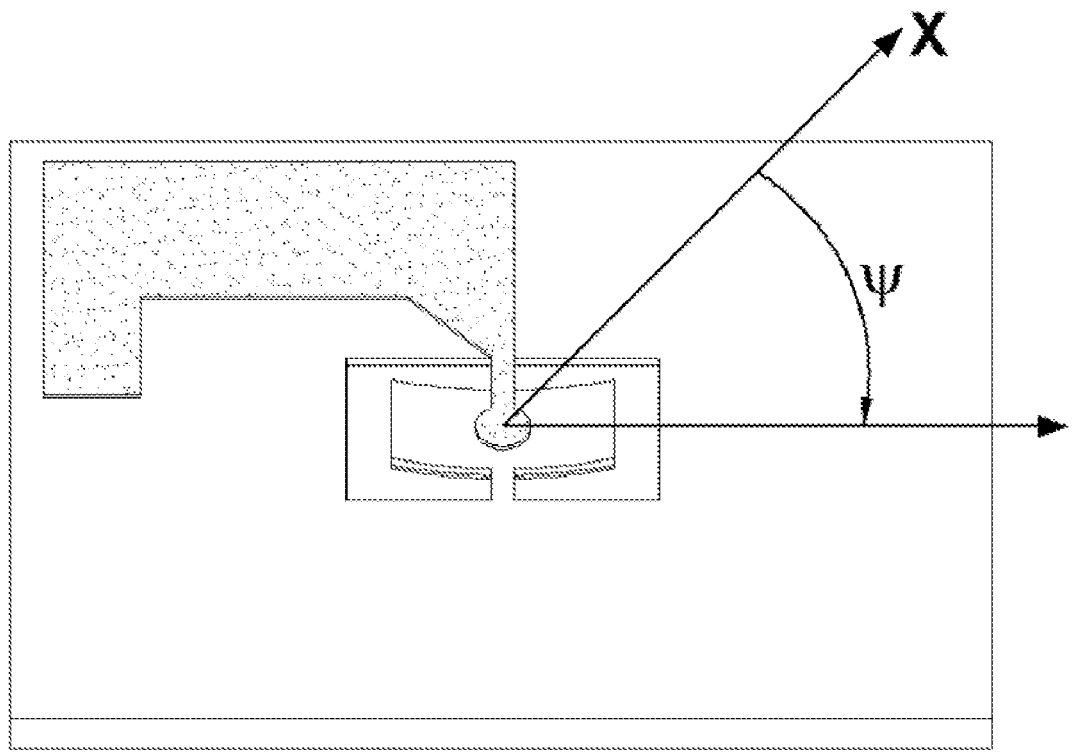
FIG. 14b shows a whole rectangle bulk acoustic wave (BAW) structure with angle alignment according to one embodiment.
Figure 14C:
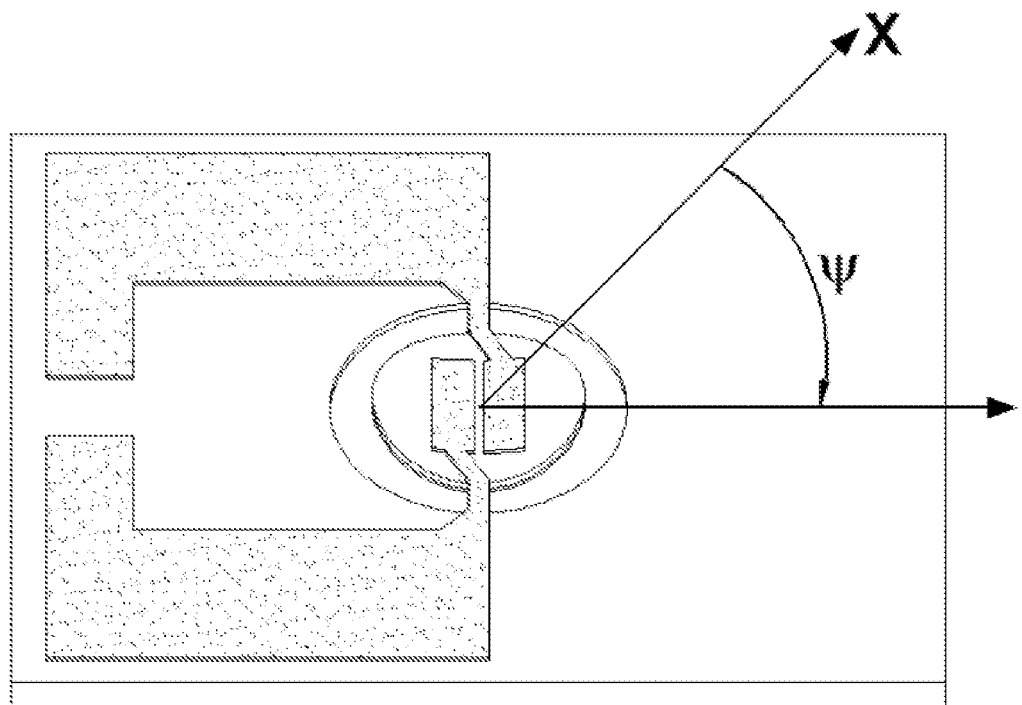
FIG. 14c shows a whole circle bulk acoustic wave (BAW) monolithic crystal filter (MCF) structure with angle alignment according to one embodiment.
Figure 14D:
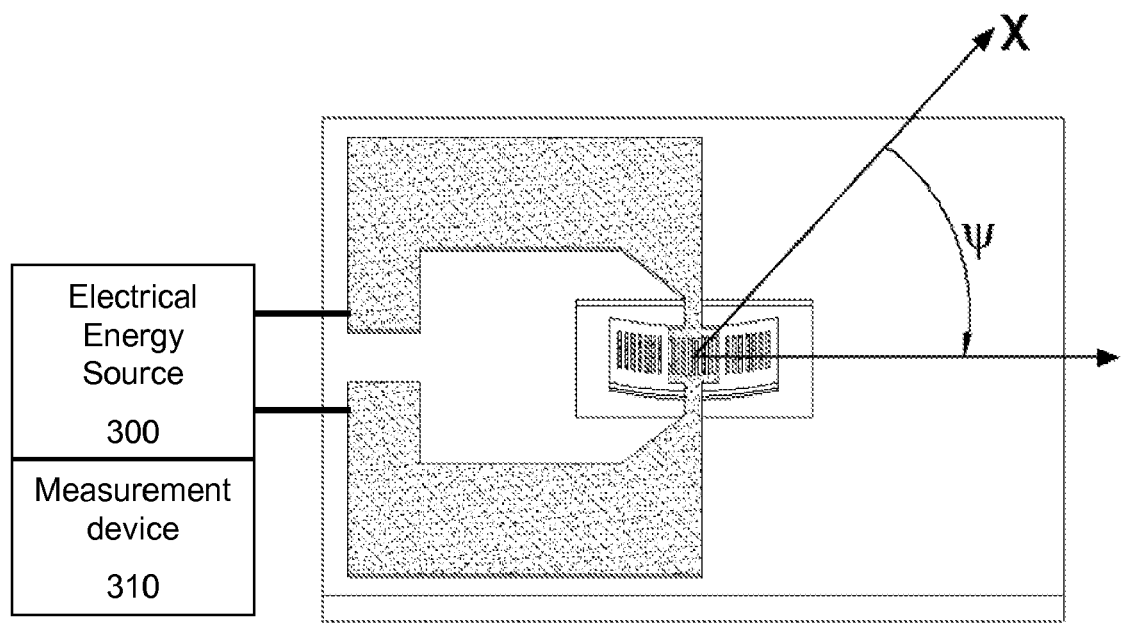
FIG. 14d shows a whole rectangle surface generated acoustic wave (SGAW) structure with angle alignment according to one embodiment.

Referring to FIGS. 14b, 14c, and 14d, these illustrate that there are angles $\psi$ relative to the crystalline axes for flexure wherein these angles will provide tailored response. According to one embodiment, the structure is designed so as to be optimized for the response curve according to the angular alignment.

For each of the designs illustrated herein, there are other variations based on the cantilever length or diameter and cantilever alignment angle with respect to the crystalline x-axis. There are two angles of interest, namely one for the cantilever device and one for the force flexure direction of the AWD, and the AWD does not have to be aligned parallel with respect to the cantilever. Thus, the $\psi$ angle of the AWD can be different than the $\psi$ angle alignment of the cantilever structure. According to one embodiment, in keeping with the separation of cantilever and AWD device design requirements, it is possible to arbitrarily align the AWD with respect to the main axes of the cantilever. There may be an optimized case for optimal sensitivity or application specific requirements.

When the rectangular or circular cantilever bends, it will cause a corresponding change in the resonant frequency or propagation or coupling characteristics of the AWD. The change in the resonant frequency or propagation or coupling characteristics of the cantilever will typically be dependent on the local curvature of the cantilever bending or "potato chipping" effect for the circular version in the confines of the supported AWD and not on the length of the cantilever or the diameter of the cantilever. This provides an advantage over other cantilever structures because the present invention is able to make cantilever structures that are much shorter in length or smaller in diameter, since no specific cantilever resonant frequency is sought. In fact, vibration insensitivity provides an incentive for very small cantilevers. This fact, in turn, allows for the creation of arrays of cantilevers in a much smaller area than other competing cantilever technologies.

A device can also incorporate the present sensing wherein the unit continuously monitors the environment and upon the triggering of a certain target matter, a notification is provided. As detailed herein, an array of cantilever sensing devices can be deployed with respective AWDs for the detection of the gas(es) for a particular film. Multiple arrays with differing designs and differing films can be encompassed within a single housing such that multiple gases can be detected.

Referring again to FIG. 14d, the coupling of the electrical energy source 300 and the measurement device 310 are depicted according to one embodiment. Electrical connectivity and the circuit configurations for generating the electrical signals and measuring responses are well known in the art, including both wired and wireless implementations. Typically there is some electrical energy signal source 300 which is then electrically coupled to the structure via electrical traces, vias, and bus bars. According to a basic example intended to show a simple embodiment, there is an electrical energy source 300 such as an oscillator circuit that provides the drive signal. The drive signal, which may be a frequency locked to the phase shift of the AWD, is coupled to the structure via the electrical connections, which in turn is electrically coupled to the corresponding electrodes of the cantilever device thereby providing the acoustic waves through the inverse piezoelectric effect. The output response is electrically coupled in a similar manner via the piezoelectric effect to the electrodes and electrical connections to a measuring device 310, which can be a frequency measuring device, monitoring the frequency at which the oscillator maintains the requisite phase shift through the AWD. The change in frequency based on movement of the cantilever can be processed to determine the effects related to the sensing film. Measurement devices are, by way of non-limiting example, devices that measure the phase, frequency, spectral signature, pulse shape, amplitude or other characteristic or modulation of the electrical signals within the AWD or presented at the electrical connections. Where the term frequency is used in conjunction with a measurement or observation it is implicit that any other characteristic of the signal could be implied. Therefore the term flexure-frequency should also be broadly construed as meaning the effect of flexure and related strain in the cantilever on any of the characteristics of the electrical signal chosen for measurement, frequency merely being one of the most widely employed characteristics in AWD sensors, which is readily apparent to one skilled in the art.

As detailed herein, there are many embodiments and applications that can be implemented using the present invention. Some of these include the following: BAW Cantilever—BAW Cantilever Gas Sensors; and BAW Cantilever Magnetic Sensors; and BAW Cantilever Torque Sensors: SGAW Cantilever-SGAW Cantilever Gas Sensors; and SGAW Cantilever Magnetic Sensors; and SGAW Cantilever Torque Sensors: MCF Cantilever—MCF Cantilever Gas Sensors; MCF Cantilever Magnetic Sensors; and MCF Cantilever Torque Sensors: LFE Cantilever—LFE Cantilever Gas Sensors; and LFE Cantilever Magnetic Sensors; and LFE Cantilever Torque Sensors: FBAR Cantilever—FBAR Cantilever Gas Sensors; and FBAR Cantilever Magnetic Sensors; and FBAR Cantilever Torque Sensors.

MEMS silicon resonators are an alternative for quartz crystals in reference oscillators, due to their compact size, low cost and feasibility of integration with IC technology. The use of MEMS resonators is within the scope of the present invention. The present invention overcomes reproducibility and manufacturability issues in MEMS cantilevers by isolating the AWD design constraints from the cantilever manufacturing control.

It should be noted that the in addition to flexure, one embodiment of the present invention functions with twist effects. The twist effects refer to an application of a load wherein the film stress is not in equilibrium. For example, the twist effect may be imparted when the tethers or supports are not symmetric as in the double-ended cantilever embodiments, such that the forces from the sensing film create a twist effect on the cantilever structure. In general, twist is a specific case of strain and that flexure and strain should be not be construed to be limited to linear or "potato chip" bending of the cantilever structure.

While the foregoing has discussed electrodes it should not be assumed that metallic electrical connections are implied. Doped semiconductors, conductive polymers and ionic conductors are all to be construed as conductive materials capable of providing electrical coupling of signals into or out of electrodes as well as to be capable of serving as the electrodes themselves. In addition, the use of terminology such as ground electrodes is merely for convention as a means of referring to a complement to a "positive" electrode and need not be connected in common and does not have to refer to a connection to earth ground.

While the foregoing has focused on sensors in which the flexure is induced due to stresses in a sensing film, other examples include the flexural vibrations of the entire cantilever caused by incident acoustic waves from the air or fluid surroundings or other external, physical properties of the environment.

It should be noted that the term "acoustic sensing" and related terms employed herein refer to the use of AWDs to sense ambient conditions and are not generally meant to infer the detection of acoustic energy, as in a hydrophone.

According to one embodiment of the invention, the cantilever is packaged in off the shelf packaging depending upon the application such as metal package, ceramic package, and all "quartz" (or other piezoelectric material) package.

The foregoing description of the embodiments of the invention has been presented for the purposes of illustration and description. It is not intended to be exhaustive or to limit the invention to the precise form disclosed. Many modifications and variations are possible in light of this disclosure. It is intended that the scope of the invention be limited not by this detailed description, but rather by the claims appended hereto.

What is claimed is:

1. A system for sensing, comprising:
a cantilever structure having a cantilever length extent and a cantilever width extent coupled to a substrate about at least one side of said cantilever, wherein said cantilever includes a piezoelectric section and has at least one acoustic wave device (AWD) on a portion of said cantilever, wherein an AWD length extent and an AWD width extent define an active acoustic region within said AWD, wherein at least one of said AWD length extent and said AWD width extent is less than at least one of said cantilever length extent and said cantilever width extent; and
wherein a flexure of said cantilever produces flexure-frequency effects measurable by said AWD whose resonance is independent of the intrinsic resonant flexural frequency of said cantilever, wherein said AWD is a bulk-generated acoustic wave (BGAW) device and operates by at least one of energy-trapping and thickness-resonance modes.

2. The system according to claim 1, further comprising a sensing material disposed on at least a portion of at least one surface of said cantilever.

3. The system according to claim 2, wherein said sensing material is selected from at least one of the group consisting of: metal, metal oxide, metal nitride, ceramic, metal carbide, polymer, fluoropolymer, silane, siloxane, silicone, and biological material.

4. The system according to claim 1, wherein said active acoustic region is a thickness field excitation (TFE) structure formed by at least one positive electrode disposed on one side of said cantilever and at least one ground electrode on an opposing side of said cantilever, and wherein an electrical energy source is coupled to said at least one positive electrode and said at least one ground electrode.

5. The system according to claim 4, wherein said thickness field excitation (TFE) structure is a two port device wherein a first transducer is electrically coupled to said electrical energy source by a positive electrical connection and a negative electrical connection and a second transducer provides a response related to the input electrical signal from said electrical energy source to a second positive electrical connection and second negative electrical connection.

6. The system according to claim 1, wherein said active acoustic region is a lateral field excitation (LFE) structure formed by at least one positive electrode and at least one negative electrode electrically coupled on one side of said cantilever and to an electrical energy source.

7. The system according to claim 1, wherein said active acoustic region is a surface generated acoustic wave (SGAW) formed by at least one transducer electrically coupled on one side of said cantilever, wherein said transducer is electrically coupled to an electrical energy source.

8. The system according to claim 7, further comprising a surface displacement medium operatively coupled with said at least one transducer, wherein said surface displacement medium is selected from the group consisting of: reflective grating, reflectionless grating, transducer, delay line, metal trapping grating, and thin film trapping layer.

9. The system according to claim 7, wherein said SGAW is a one port device wherein a single said transducer is electrically coupled to said electrical energy source by a positive electrical connection and a negative electrical connection.

10. The system according to claim 7, wherein said SGAW is a two port device wherein said first transducer is electrically coupled to said electrical energy source by a positive electrical connection and a negative electrical connection and said second transducer provides a response related to said input signal from said electrical energy source to a second positive electrical connection and second negative electrical connection.

11. The system according to claim 1, wherein a shape of said cantilever is selected from at least one of the group consisting of: rectangular whole, rectangular half, square whole, square half, circular whole, circular half, oval whole, oval half, triangular whole, triangular half, polygonic whole and polygonic half.

12. The system according to claim 1, wherein said cantilever is coupled to said substrate by one of the group consisting of: single tether, single fixed support, dual tether, and dual fixed support.

13. The system according to claim 1, further comprising a measurement device coupled to said AWD and measuring said flexure-frequency effects.

14. A method for detecting a target substance, comprising:
forming a piezoelectric cantilever having a cantilever length extent and a cantilever width extent and having at least one acoustic wave device (AWD) disposed about a portion of said cantilever, wherein an AWD length extent and an AWD width extent define an active acoustic region within said AWD, wherein at least one of said AWD length extent and said AWD width extent is less than at least one of said cantilever length extent and said cantilever width extent;
exposing said cantilever structure to some environment;
causing a flexure response of said cantilever from said environment; and
detecting a response of said AWD whose resonance is independent of the intrinsic resonant flexural frequency of said cantilever, wherein said AWD is a bulk-generated acoustic wave (BGAW) device and operates by at least one of energy-trapping and thickness-resonance modes.

15. The method according to claim 14, further comprising disposing a sensing material on at least one portion of said cantilever and allowing adsorption/absorption of said target substance by said sensing material.

16. The method according to claim 14, further comprising aligning said AWD at an angle ($\psi$) with respect to the cantilever for a maximum change in frequency.

17. A sensing device for measuring flexure-frequency effects, comprising:
a substrate having electrical connections disposed about said substrate and providing connectivity to an electrical energy signal and a measurement device;
a cantilever having a cantilever length extent and a cantilever width extent and coupled on at least one side to said substrate, said cantilever comprising:
at least one acoustic wave device (AWD) formed on a portion of said cantilever, said AWD comprising a piezoelectric section and having at least two electrodes disposed thereon,
wherein an AWD length extent and an AWD width extent define an active acoustic region within said AWD, wherein at least one of said AWD length extent and said AWD width extent is less than at least one of said cantilever length extent and said cantilever width extent,
wherein a flexure of said cantilever causes a change of a response of said AWD to said electrical energy signal that is measurable by said measurement device, and
wherein resonance of said AWD is independent of the intrinsic resonant flexural frequency of said cantilever, wherein said AWD is a bulk-generated acoustic wave (BGAW) device and operates by at least one of energy-trapping and thickness-resonance modes.

18. The device according to claim 17, further comprising a sensing material disposed on at least a portion of at least one surface of said cantilever.

19. The device according to claim 17, wherein the sensing device is selected from at least one of the group consisting of: bulk acoustic wave (BAW) cantilever gas sensors, BAW cantilever magnetic sensors, BAW cantilever torque sensors, monolithic crystal filter (MCF) cantilever gas sensors, MCF cantilever magnetic sensors, MCF cantilever torque sensors, film bulk acoustic resonator (FBAR) cantilever gas sensors, FBAR magnetic sensors, and FBAR torque sensors.

20. The device of claim 17, wherein the piezoelectric section is selected from the group consisting of quartz, lithium niobate, lithium tantalate, langasite, langanite, langatate, aluminum phosphate, gallium phosphate, calcium/strontium niobium/tantalum gallium silicate (CNGS, CTGS, SNGS, STGS), zinc oxide, aluminum nitride and compositions and combinations thereof.

21. A system for acoustic sensing, comprising:
a cantilever structure having a cantilever length extent and a cantilever width extent and coupled to a substrate about at least one side of said cantilever, wherein said cantilever includes a piezoelectric section and having at least one acoustic wave device (AWD),
wherein an AWD length extent and an AWD width extent define an active acoustic region within said AWD, wherein at least one of said AWD length extent and said AWD width extent is less than at least one of said cantilever length extent and said cantilever width extent,
wherein the design requirements of said AWD are independent of the design of said cantilever, wherein said AWD is a bulk-generated acoustic wave (BGAW) device and operates by at least one of energy-trapping and thickness-resonance modes;
an electrical signal coupled to said cantilever structure;
wherein a flexure of said cantilever produces flexure-frequency effects on a response of said AWD to said electrical signal; and
wherein said flexure-frequency effects induce modulation of the electrical signal.

* * * * *